US010144727B2

(12) United States Patent
Ramstedt et al.

(10) Patent No.: US 10,144,727 B2
(45) Date of Patent: Dec. 4, 2018

(54) DEOXYNOJIRIMYCIN DERIVATIVES AND METHODS OF THEIR USING

(71) Applicant: Emergent Virology LLC, Gaithersburg, MD (US)

(72) Inventors: Urban Ramstedt, Bethesda, MD (US); Raju Penmasta, Herndon, VA (US); Hitesh Batra, Herndon, VA (US); Tam Nguyen, Gaithersburg, MD (US)

(73) Assignee: Emergent Virology LLC, Gaithersburg, MD (US)

( * ) Notice: Subject to any disclaimer, the term of this patent is extended or adjusted under 35 U.S.C. 154(b) by 120 days.

(21) Appl. No.: 15/022,005

(22) PCT Filed: Sep. 15, 2014

(86) PCT No.: PCT/US2014/055599
§ 371 (c)(1),
(2) Date: Mar. 15, 2016

(87) PCT Pub. No.: WO2015/039010
PCT Pub. Date: Mar. 19, 2015

(65) Prior Publication Data
US 2016/0221993 A1    Aug. 4, 2016

Related U.S. Application Data

(60) Provisional application No. 61/878,286, filed on Sep. 16, 2013.

(51) Int. Cl.
*C07D 405/06* (2006.01)
*C07D 211/46* (2006.01)
*C07D 211/40* (2006.01)

(52) U.S. Cl.
CPC .......... *C07D 405/06* (2013.01); *C07D 211/40* (2013.01); *C07D 211/46* (2013.01)

(58) Field of Classification Search
None
See application file for complete search history.

(56) References Cited

U.S. PATENT DOCUMENTS

| | | |
|---|---|---|
| 4,246,345 A | 1/1981 | Kinast et al. |
| 4,266,025 A | 5/1981 | Kinast et al. |
| 4,405,714 A | 9/1983 | Kinast et al. |
| 4,806,650 A | 2/1989 | Schroeder et al. |
| 4,994,572 A | 2/1991 | Fleet |
| 5,043,273 A | 8/1991 | Scudder et al. |
| 5,103,008 A | 4/1992 | Scudder et al. |
| 5,200,523 A | 4/1993 | Fleet |
| 5,622,972 A | 4/1997 | Bryant et al. |
| 6,465,487 B1 | 10/2002 | Block et al. |
| 6,545,021 B1 | 4/2003 | Mueller et al. |
| 6,689,759 B1 | 2/2004 | Jacob et al. |
| 6,809,803 B1 | 10/2004 | O'Brien et al. |
| 7,256,005 B2 | 8/2007 | Zitzmann et al. |
| 7,612,093 B2 | 11/2009 | Jacob et al. |
| 7,816,650 B2 | 10/2010 | Gat et al. |
| 8,426,445 B2 | 4/2013 | Ramstedt et al. |
| 8,450,345 B2 | 5/2013 | Ramstedt et al. |
| 9,044,470 B2 | 6/2015 | Ramstedt et al. |
| 2007/0275998 A1 | 11/2007 | Butters et al. |
| 2008/0138351 A1 | 6/2008 | Dwek et al. |
| 2009/0042268 A1 | 2/2009 | Gu et al. |
| 2009/0252785 A1 | 10/2009 | Pollock et al. |
| 2010/0222383 A1* | 9/2010 | Ramstedt ............. A61K 31/445 514/315 |
| 2010/0222384 A1 | 9/2010 | Ramstedt et al. |
| 2010/0266678 A1 | 10/2010 | Pollock et al. |
| 2011/0065752 A1 | 3/2011 | Ramstedt et al. |
| 2011/0065753 A1 | 3/2011 | Ramstedt et al. |
| 2011/0065754 A1 | 3/2011 | Ramstedt et al. |
| 2011/0184019 A1 | 7/2011 | Zitzmann et al. |

(Continued)

FOREIGN PATENT DOCUMENTS

| WO | WO-2010096764 A1 | 8/2010 |
|---|---|---|
| WO | WO-2011028775 A1 | 3/2011 |
| WO | WO-2011028781 A1 | 3/2011 |
| WO | WO-2014017915 A2 | 1/2014 |

OTHER PUBLICATIONS

Berge, S.M., et al., "Pharmaceutical Salts," Journal of Pharmaceutical Sciences 66(1):1-19, Wiley, United States (1977).
International Search Report and Written Opinion for International Application No. PCT/US2014/055599, ISA/US Alexandria, Virginia, dated Feb. 25, 2015, 12 pages.
Kato, E., et al., "Synthesis and α-amylase Inhibitory Activity of Glucose-deoxynojirimycin Conjugates," Tetrahedron 67(40):7692-7702, Elsevier Ltd., England (2011).
Prestwood, T.R., et al., "Gamma Interferon (IFN-γ) Receptor Restricts Systemic Dengue Virus Replication and Prevents Paralysis in IFN-α/β Receptor-deficient Mice," Journal of Virology 86(23):12561-12570, American Society for Microbiology, United States (2012).
Pubchem, Open Chemistry Database, "Compound Summary for CID 503982, UNII-3P161BU63E," accessed at hhttps://pubchem.ncbi.nlm.nih.gov/compound/503982?from=summary, created on Aug. 1, 2005, 15 pages.

(Continued)

*Primary Examiner* — Leslie A. Royds Draper
(74) *Attorney, Agent, or Firm* — Sterne, Kessler, Goldstein & Fox P.L.L.C.

(57) ABSTRACT

The present application provide novel iminosugars and their use in treatment of viral infections, such as Dengue infection and Influenza A infection. The present inventors discovered certain deoxynojirimycin derivatives may be effective against one or more viruses, which may be, for example, a Dengue virus and/or a virus belonging to the Orthomyxoviridae family, such as an Influenza A virus. In particular, such deoxynojirimycin derivatives may be useful for treating a disease or condition caused by or associated with one or more viruses. In certain embodiments, the deoxynojirimycin derivatives may increase a survival rate or probability for a subject infected with one or more viruses, which may be, for example, a Dengue virus and/or a virus belonging to the Orthomyxoviridae family, such as an Influenza A virus.

12 Claims, 19 Drawing Sheets

(56) References Cited

U.S. PATENT DOCUMENTS

Figure 1:
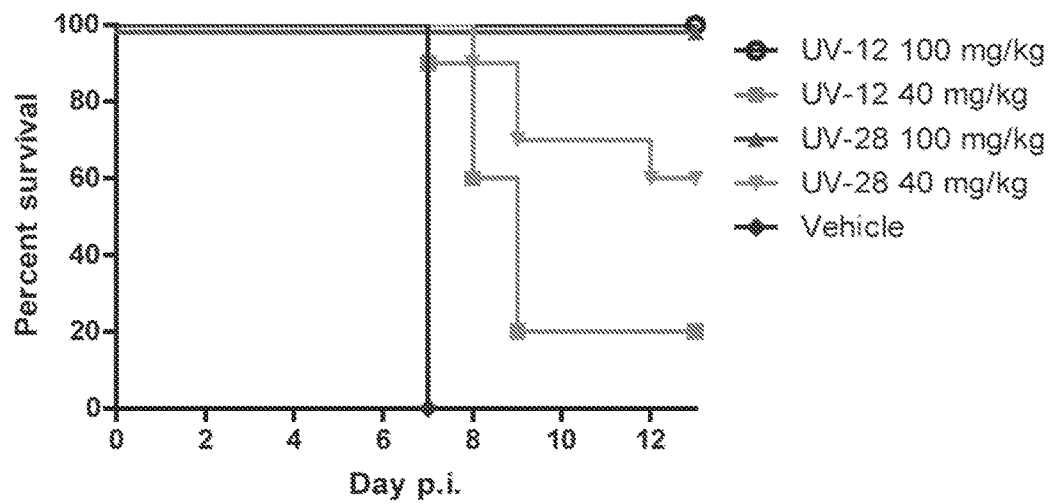

2011/0189771 A1 8/2011 Block et al.
2013/0150405 A1 6/2013 Ramstedt et al.

OTHER PUBLICATIONS

Zellweger, R.M., et al., "Enhanced Infection of Liver Sinusoidal Endothelial Cells in a Mouse Model of Antibody-induced Severe Dengue Disease," Cell Host & Microbe 7(2):128-139, Elsevier Inc., United States (2010).

Yu, W., et al., "Design, synthesis, and biological evaluation of N-alkylated deoxynojirimycin (DNJ) derivatives for the treatment of dengue virus infection," Journal of Medicinal Chemistry 55(13):6061-6075, American Chemical Society, United States (2012).

Extended European Search Report for EP Application No. 14844653.7, European Patent Office, Munich, Germany, dated May 9, 2017, 9 pages.

Mehta, A., et al., "Imino sugars that are less toxic but more potent as antivirals, in vitro, compared with N-n-nonyl DNJ," Antiviral Chemistry & Chemotherapy 13:299-304, International Medical Press, England (2002).

Miller, J.L., et al., "Liposome-mediated delivery of iminosugars enhances efficacy against dengue virus in vivo," Antimicrobial Agents and Chemotherapy 56(12):6379-6386, American Society for Microbiology, United States (2012).

Perry, S.T., et al., "An iminosugar with potent inhibition of dengue virus infection in vivo," Antiviral Research 98(1):35-43, Elsevier B.V., Netherlands (2013).

* cited by examiner

| | 100 mg/kg UV-4B | 100 mg/kg UV-8 | 100 mg/kg UV-9 | 100 mg/kg UV-10 | 100 mg/kg UV-11 | 100 mg/kg UV-12 |
|---|---|---|---|---|---|---|
| Treated samples vs H2O Control Group | | | | | | |
| Log-rank (Mantel-Cox) Test | | | | | | |
| Chi square | 9.429 | 0.2812 | 8.043 | 2.924 | 2.66 | 8.272 |
| df | 1 | 1 | 1 | 1 | 1 | 1 |
| P value | 0.0021 | 0.5959 | 0.0046 | 0.0873 | 0.1029 | 0.004 |
| P value summary | ** | ns | ** | ns | ns | ** |
| Significant? | Yes | No | Yes | No | No | Yes |
| Gehan-Breslow-Wilcoxon Test | | | | | | |
| Chi square | 8.978 | 0.9379 | 7.335 | 2.41 | 1.261 | 8.565 |
| df | 1 | 1 | 1 | 1 | 1 | 1 |
| P value | 0.0027 | 0.3328 | 0.0068 | 0.1206 | 0.2614 | 0.0034 |
| P value summary | ** | ns | ** | ns | ns | ** |
| Significant? | Yes | No | Yes | No | No | Yes |
| Median survival | | | | | | |
| Control + H2O | 9 | 9 | 9 | 9 | 9 | 9 |
| Treated Group | Undefined | 10.5 | 7 | 7.5 | 8 | Undefined |
| Hazard Ratio | | | | | | |
| Ratio | 11.79 | 1.369 | 0.1389 | 0.3758 | 0.3845 | 8.977 |
| 95% CI of ratio | 2.441 to 56.96 | 0.4286 to 4.373 | 0.03550 to 0.5435 | 0.1224 to 1.154 | 0.1219 to 1.213 | 2.012 to 40.05 |

Figure 7

| 100 mg/kg UV-4B | | |
|---|---|---|
| Source of Variation | % of Total Variation | P Value |
| Interaction | 5.9 | < 0.0001 |
| Time | 77.65 | < 0.0001 |
| Treatment | 5.16 | 0.0008 |
| Subjects (matching) | 5.7963 | < 0.0001 |

| 100 mg/kg UV-8 | | |
|---|---|---|
| Source of Variation | % of Total Variation | P Value |
| Interaction | 0.19 | 0.8896 |
| Time | 81.29 | < 0.0001 |
| Treatment | 0.26 | 0.502 |
| Subjects (matching) | 10.1209 | < 0.0001 |

| 100 mg/kg UV-12 | | |
|---|---|---|
| Source of Variation | % of Total Variation | P Value |
| Interaction | 12.31 | < 0.0001 |
| Time | 71.47 | < 0.0001 |
| Treatment | 5.25 | 0.0004 |
| Subjects (matching) | 5.1095 | < 0.0001 |

Figure 9

| 100 mg/kg UV-4B | | |
|---|---|---|
| Source of Variation | % of Total Variation | P Value |
| Interaction | 19.46 | < 0.0001 |
| Time | 29.22 | < 0.0001 |
| Treatment | 22.78 | < 0.0001 |
| Subjects (matching) | 7.9206 | < 0.0001 |

| 100 mg/kg UV-8 | | |
|---|---|---|
| Source of Variation | % of Total Variation | P Value |
| Interaction | 0.77 | 0.9137 |
| Time | 47.47 | < 0.0001 |
| Treatment | 1.74 | 0.145 |
| Subjects (matching) | 13.5295 | 0.001 |

| 100 mg/kg UV-12 | | |
|---|---|---|
| Source of Variation | % of Total Variation | P Value |
| Interaction | 23.23 | < 0.0001 |
| Time | 32.8 | < 0.0001 |
| Treatment | 13.33 | < 0.0001 |
| Subjects (matching) | 5.2539 | 0.1205 |

Figure 11

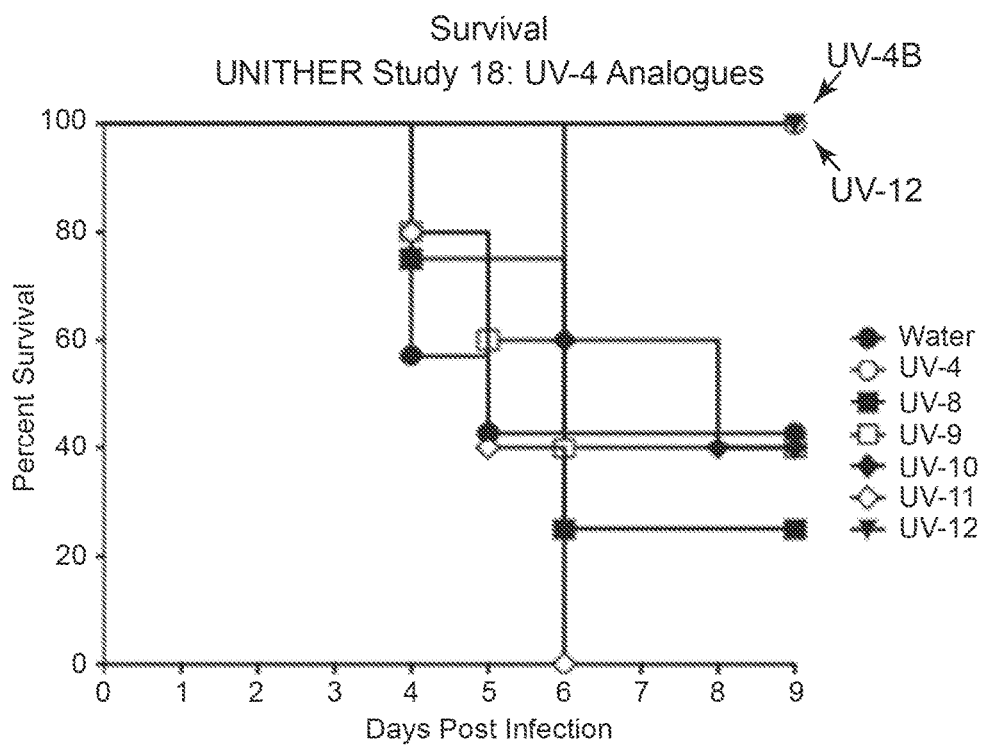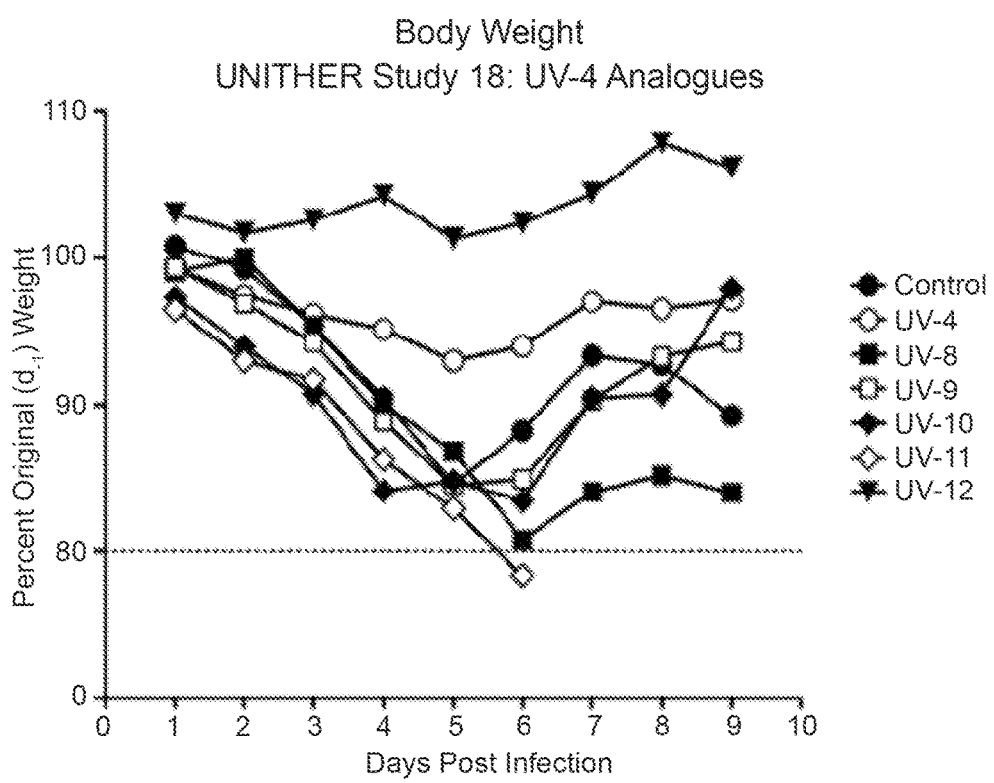
Figure 12

DEOXYNOJIRIMYCIN DERIVATIVES AND METHODS OF THEIR USING

FIELD

The present invention relates generally to iminosugars and their methods of use and in particular, to N-substituted deoxynojirimycin compounds and their use for treating and/or preventing viral infections.

SUMMARY

One embodiment is a compound of formula (I):

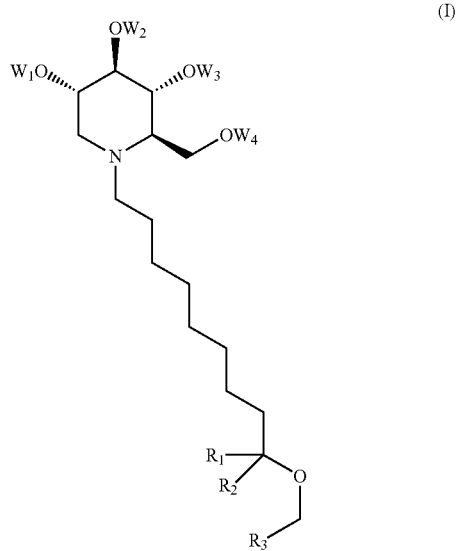

or a pharmaceutically acceptable salt thereof, wherein $W_{1-4}$ and $R_{1-3}$ are each independently selected from hydrogen and $C_{1-3}$ alkyl groups and wherein at least one of $R_{1-3}$ is not hydrogen.

Yet another embodiment is a method of treating a disease or condition caused by or associated with a virus belonging to the Orthomyxoviridae family comprising administering to a subject in need thereof the compound of formula (I) or a pharmaceutically acceptable salt thereof.

And yet another embodiment is a method of treating a disease or condition caused by or associated with Dengue virus comprising administering to a subject in need thereof the compound of formula (I) or a pharmaceutically acceptable salt thereof.

FIGURES

FIG. 1: Survival of infected mice grouped by treatment. Groups of mice (n=10) received the treatment TID starting 1 hour prior to infection; Mice were infected intranasally with influenza at a dose of ~1LD90. Survival data is plotted as percent survival against days post infection. Graph shows survival of animals in each group.

Figure 2:
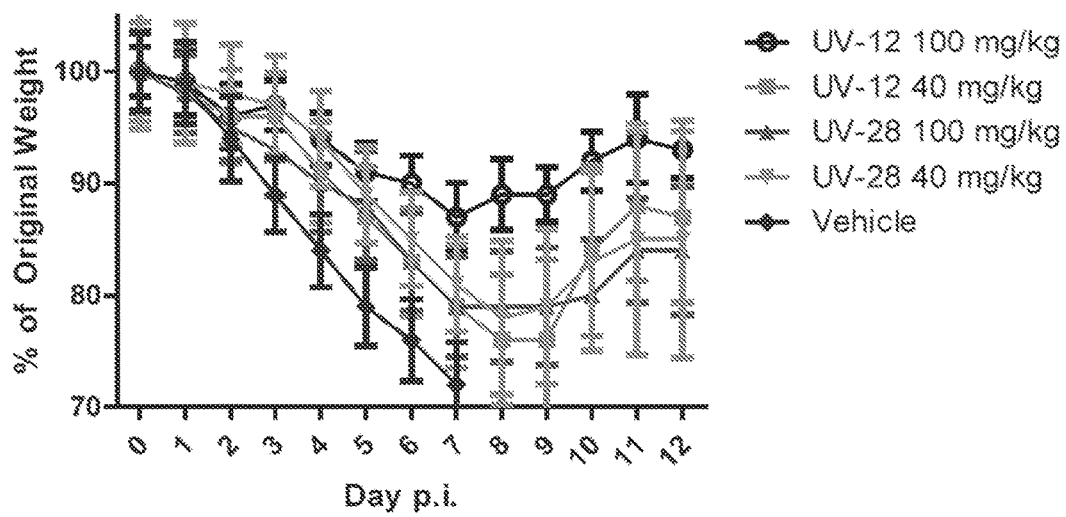

FIG. 2: Weights of infected mice grouped by treatment. Groups of mice (n=10) received the treatment TID starting 1 hour prior to infection; Mice were infected intranasally with influenza at a dose of ~$1LD_{90}$. Weight data is plotted as percent of original weight against days post infection.

Figure 3:
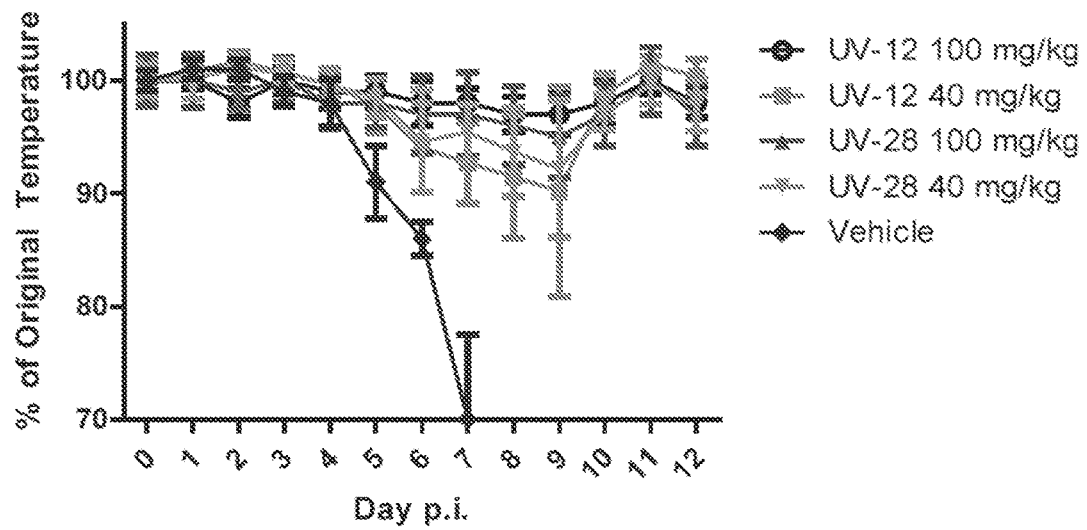

FIG. 3: Temperatures of infected mice grouped by treatment. Groups of mice (n=10) received the treatment TID starting 1 hour prior to infection; Mice were infected intranasally with influenza at a dose of ~$1LD_{90}$. Temperature data is plotted as percent of original temperature against days post infection.

Figure 4:
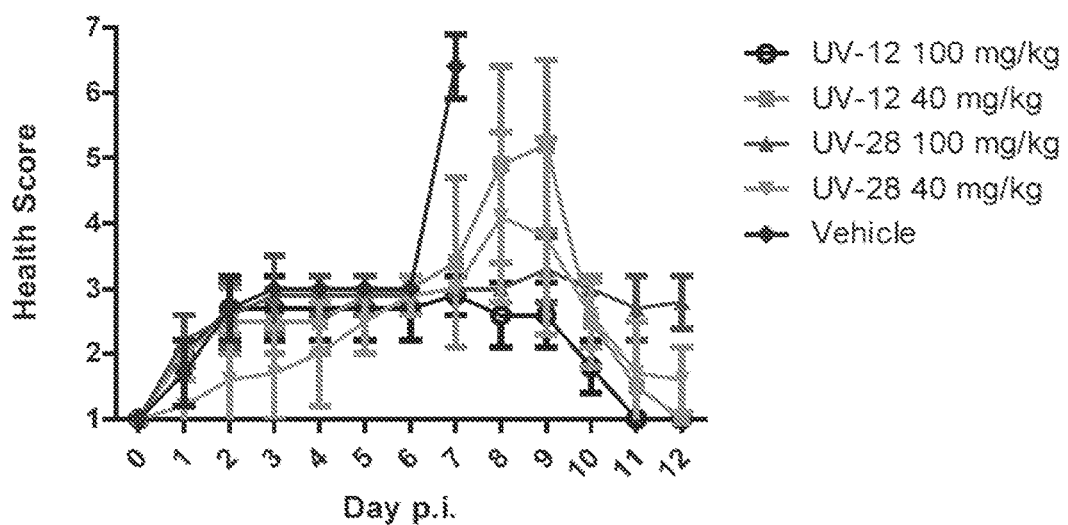

FIG. 4: Health scores of infected mice grouped by treatment. Groups of mice (n=10) received the treatment TID starting 1 hour prior to infection; Mice were infected intranasally with influenza at a dose of ~1LD90. Health data is plotted as health score vs days post infection.

Figure 5:
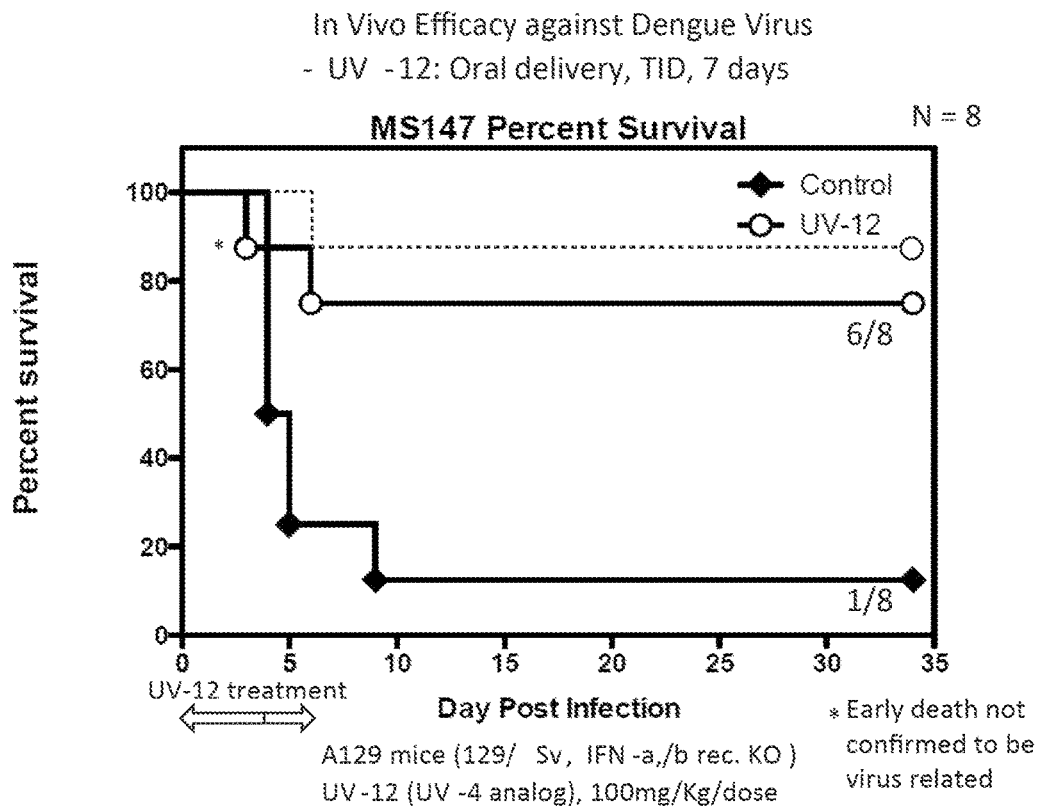

FIG. 5 presents a plot demonstrating in vivo efficacy of UV-12 against dengue virus.

Figure 6:
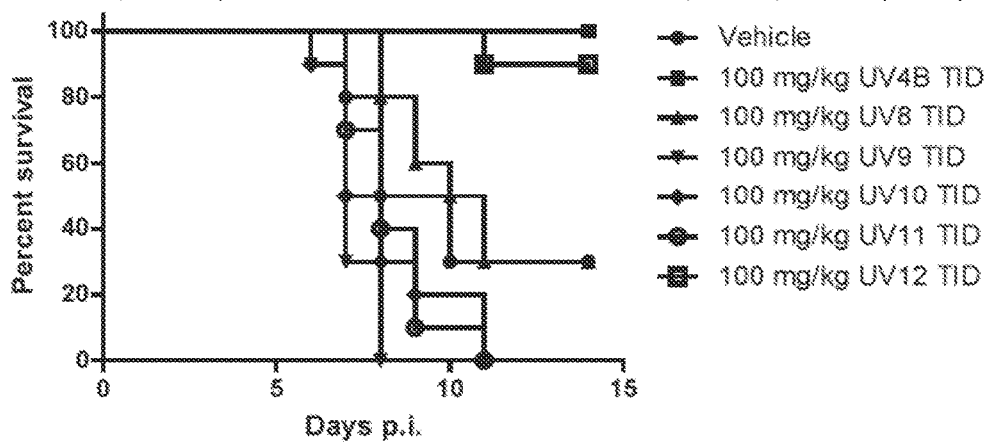
Figure 8A:
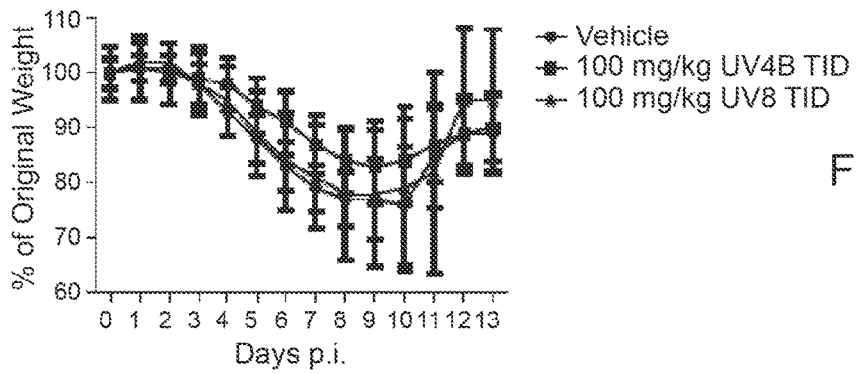
Figure 8B:
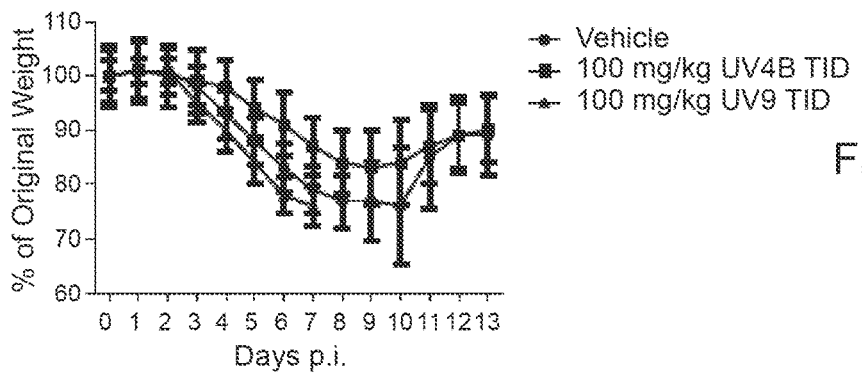
Figure 8C:
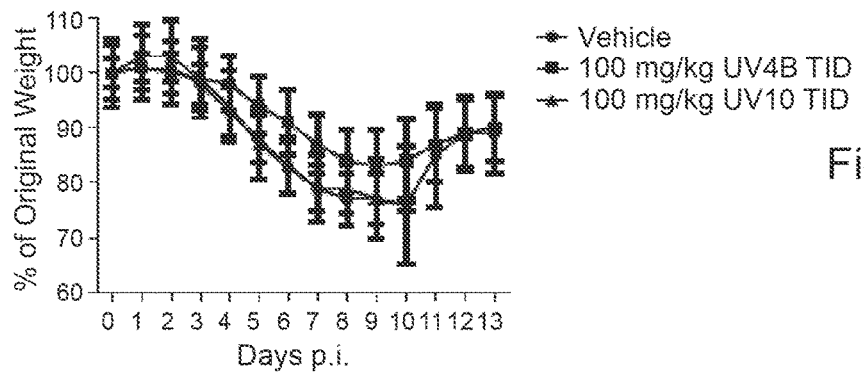
Figure 8D:
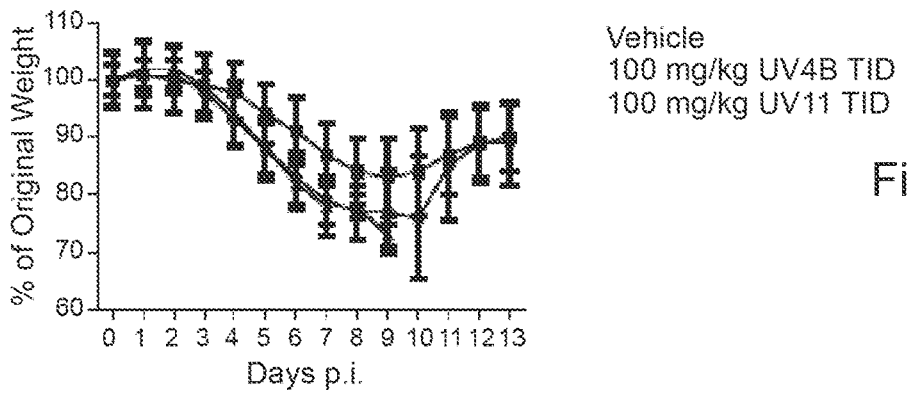
Figure 8E:
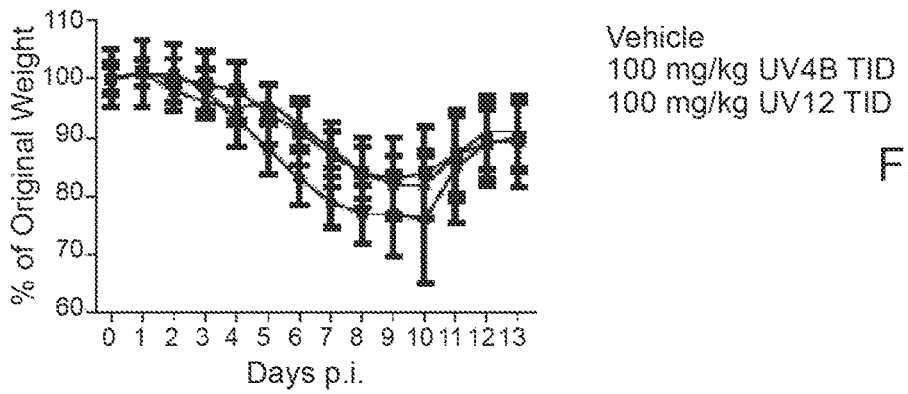
Figure 8F:
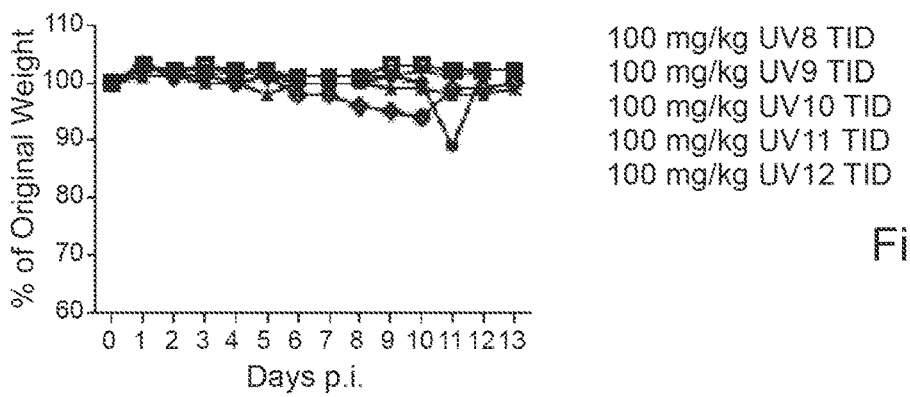
Figure 10A:
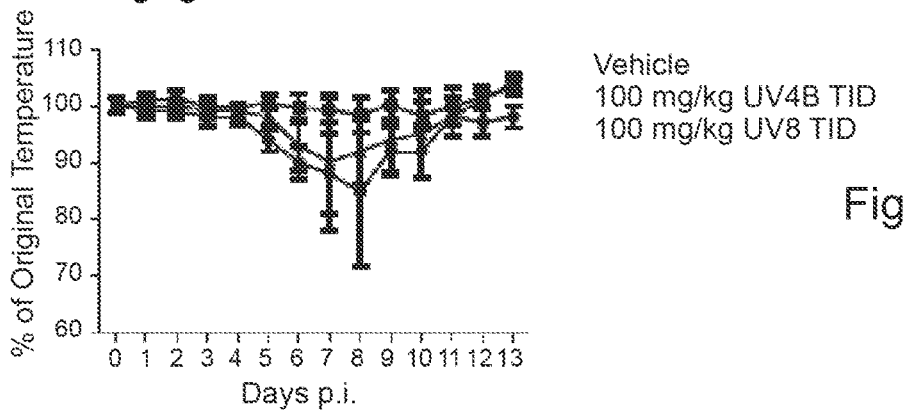
Figure 10B:
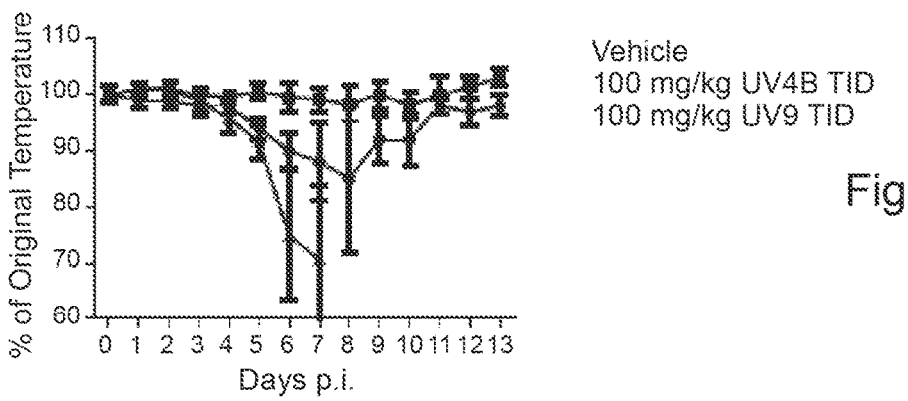
Figure 10C:
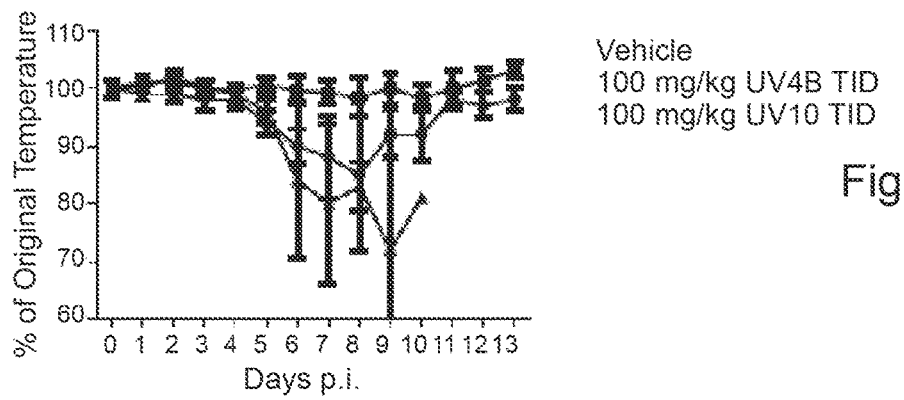
Figure 10D:
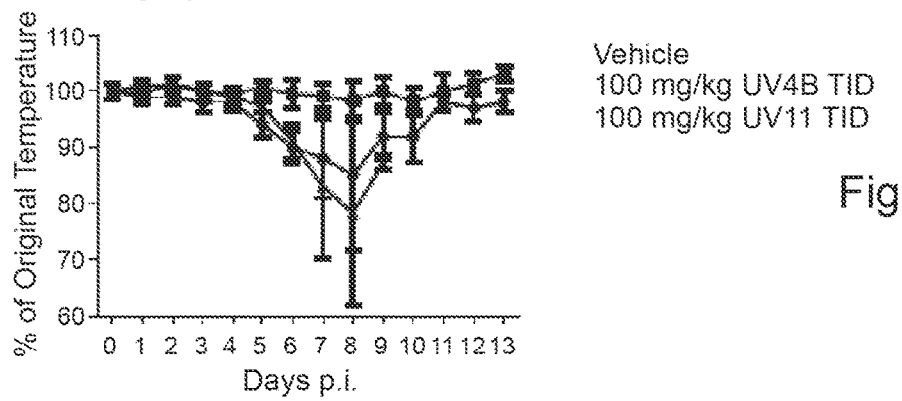
Figure 10E:
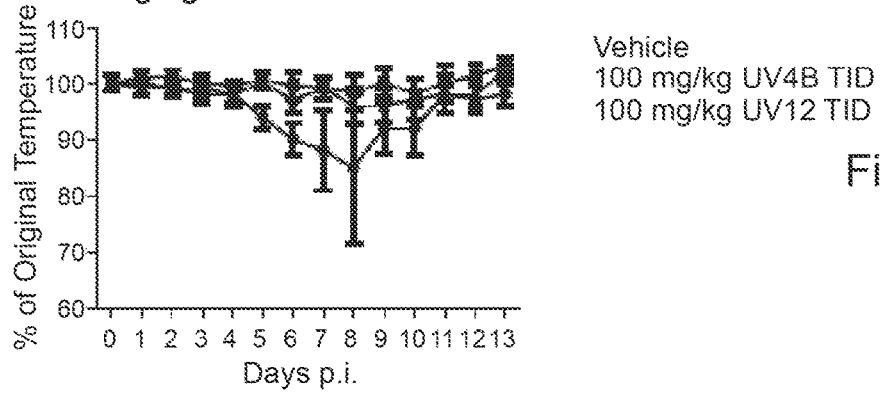
Figure 10F:
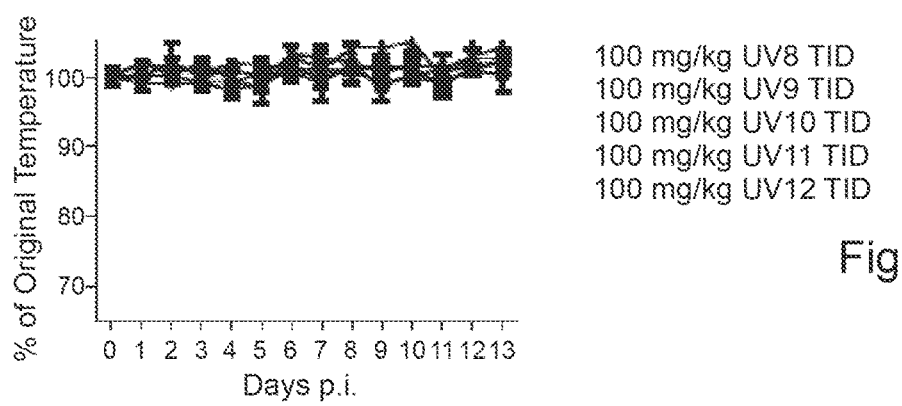

FIG. 6: Survival of mice grouped by treatment deliver) route. Groups of mice (n=10) received the first treatment dose of compound in water 1 h before an intranasal infection with Influenza A/Texas/36/91 (H1N1) at a dose of ~$1LD_{90}$. Survival data is plotted as percent survival against days post infection. (A) Treatment of 100 mg/kg of UV-4B, UV-8. UV-9. UV-10, UV-11, and UV-12, assuming a starting weight of ~20 g per mouse. Graph includes survival curve of vehicle only control group.

FIG. 7: Statistical analysis of survival of infected mice. The survival data plotted in FIG. 6 were analyzed using the Mantel-Cox and Gehan-Breslow-Wilcoxon tests. (A) Statistical analysis is by comparing the treated groups to the H2O vehicle control. Statistical significance is indicated by a p value <0.05.

FIGS. 8A-F: Analysis of Weights. Mice received the first dose of compound in H2O at 1 hour prior to the intranasal infection with ~$1LD_{90}$ of Influenza A/Texas/36/91 (H1N1). The mean weights for each group are plotted as percent of the weight on day 0 (baseline) with the standard deviations. (A) Treatment of infected mice with UV-4B or UV-8, (B) treatment of infected mice with UV-4B or UV-9, (C) treatment of infected mice with UV-4B or UV-10, (D) treatment of infected mice with UV-4B or UV-11, (E) treatment of infected mice with UV-4B or UV-12, and (F) treatment of uninfected mice with UV-8, -9, -10, -11, or -12, without standard deviations.

FIG. 9: Statistical analysis of weight data. The weight data for the influenza infected mice plotted in FIG. 8 were analyzed using a repeated-measures 2-way ANOVA (GraphPad Prism) against the vehicle control. Data was only analyzed through day 7 post-infection (p.i.) due to deaths at later time points. Compounds UV-9, UV-10, and UV-11 had both 0% survival and a MTD<9 days and were thus omitted from further statistical analysis. Statistical significance is indicated by a p value lower than 0.05 (p<0.05).

FIG. 10: Analysis of Temperatures. Mice received the first dose of compound in H2O at 1 hour prior to the intranasal infection with ~1LD90 of Influenza A/Texas/36/91 (H1N1). The mean temperatures for each group are plotted as percent of the weight on day 0 (baseline) with the standard deviations. (A) Treatment of infected mice with UV-4B or UV-8, (B) treatment of infected mice with UV-4B or UV-9, (C) treatment of infected mice with UV-4B or UV-10, (D) treatment of infected mice with UV-4B or UV-11, (E) treatment of infected mice with UV-4B or UV-12, and (F) treatment of uninfected mice with UV-8, -9, -10, -11, or -12, without standard deviations.

FIG. 11: Statistical analysis of temperature data. The temperature data for the influenza infected mice plotted in FIG. 10 were analyzed using a repeated-measures 2-way ANOVA (GraphPad Prism) against the vehicle control. Data was only analyzed through day 7 post-infection (p.i.) due to deaths at later time points. Compounds UV-9, UV-10, and UV-11 had both 0% survival and a MTD<9 days and were thus omitted from further statistical analysis. Statistical significance is indicated by a p value lower than 0.05 (p<0.05)

FIG. 12 present results of the study performed in Example 4. This study was determining survival of dengue virus infected mice. The survival data and animal body weight are plotted in FIG. 12. All compounds were given in water by the oral route (3× per day intragastric via oral gavage—IG) for a total number of 7 days after the start of dosing. The treatment dose was 50 mg/kg of UV-4B, UV-8, UV-9, UV-10, UV-11, and UV-12. Groups of mice received the first treatment dose of compound 0.5-1 h before an intravenous infection with dengue virus at a dose of ~1LD$_{90}$. Survival and body weights were measured until 3 days after dosing.

Figure 13:
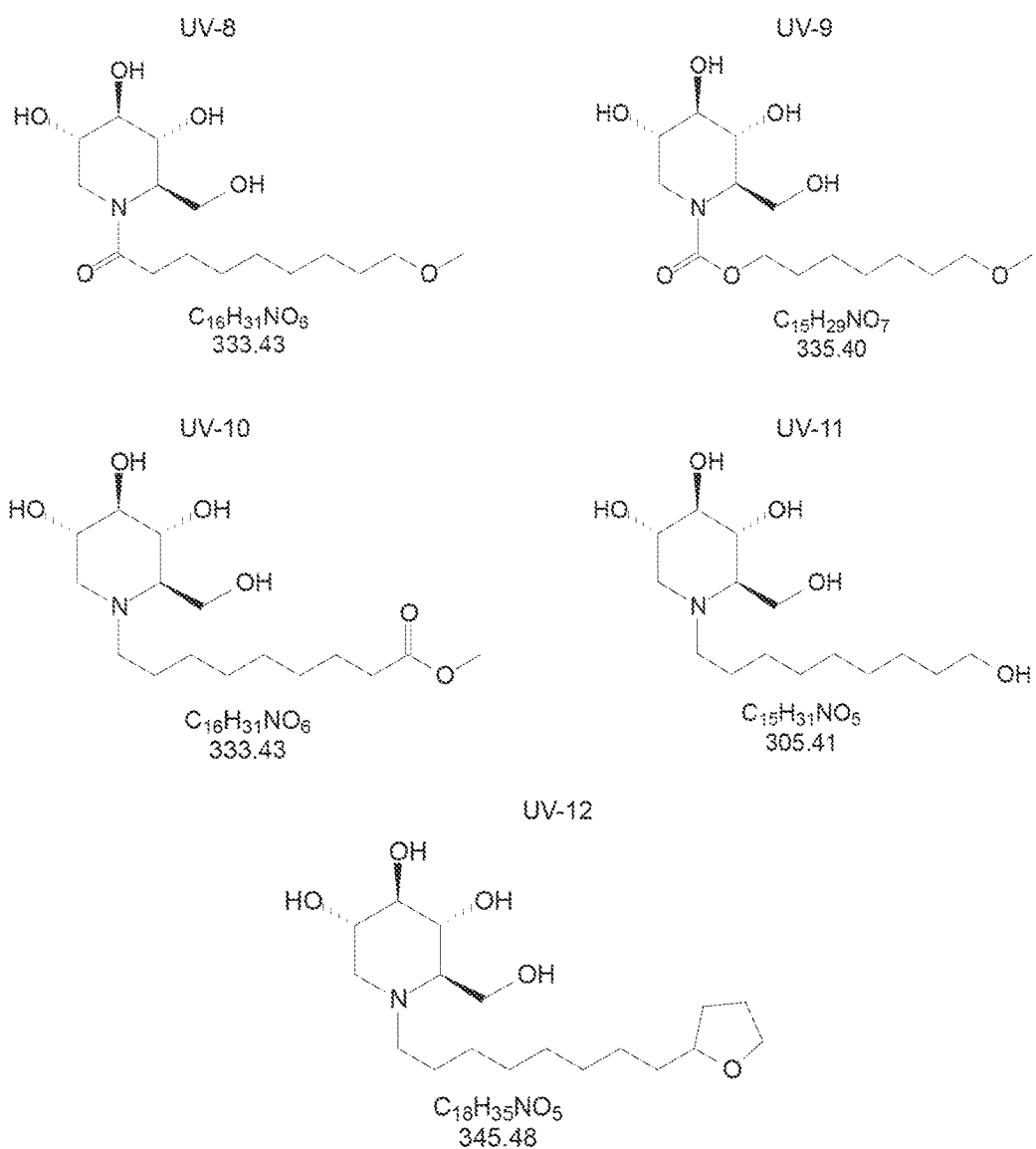

FIG. 13 presents chemical formulae of UV-8, UV-9, UV-10, UV-11 and UV-12 compounds.

Figure 14:
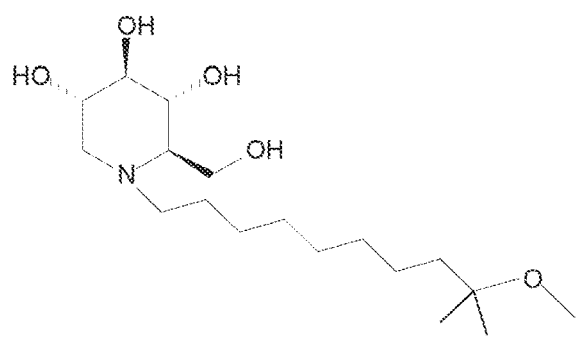

FIG. 14 presents chemical formula of UV-28.

Figure 15:
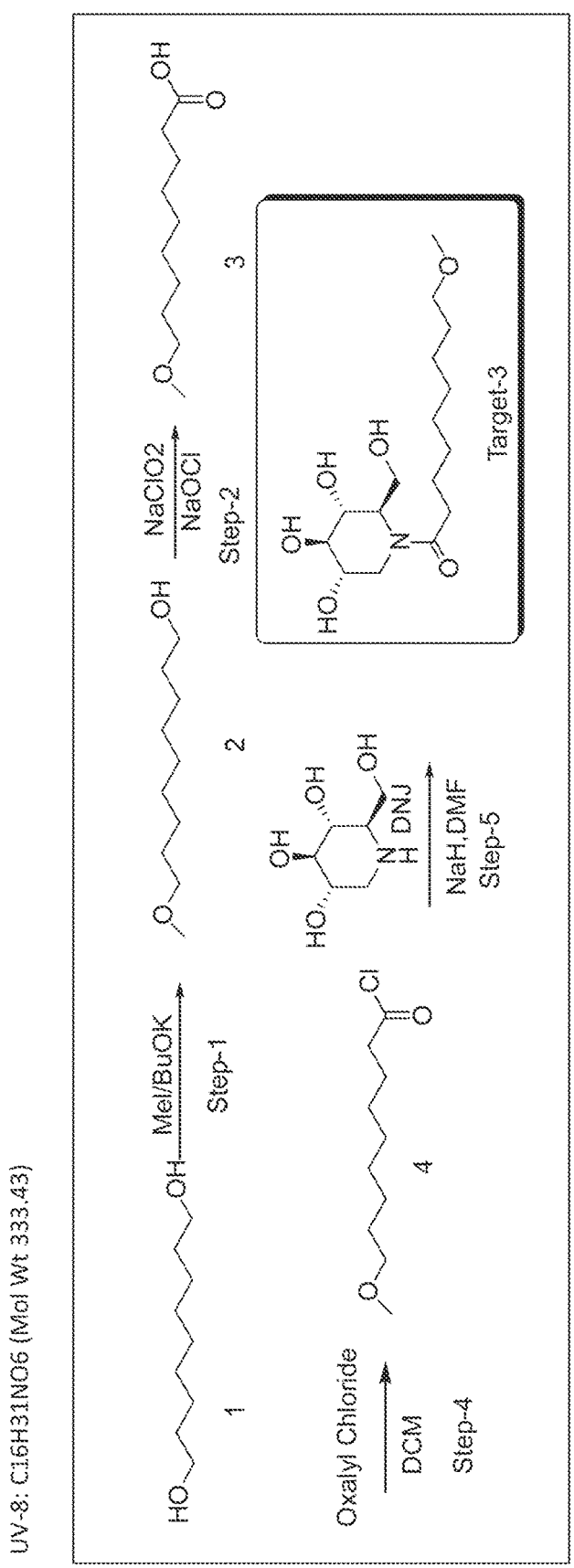

FIG. 15 provides a synthesis scheme for UV-8.

Figure 16:
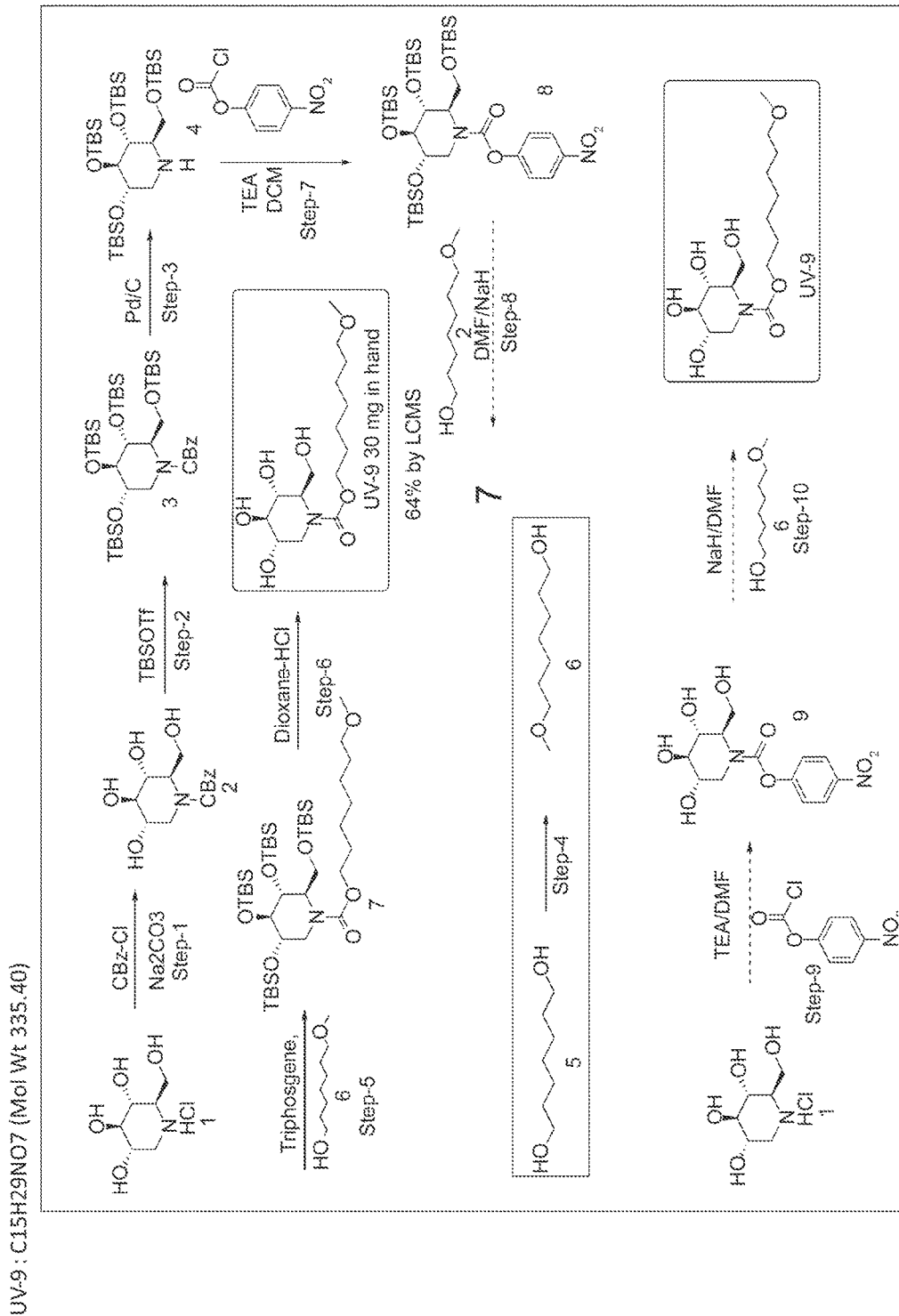

FIG. 16 provides a synthesis scheme for UV-9.

Figure 17:
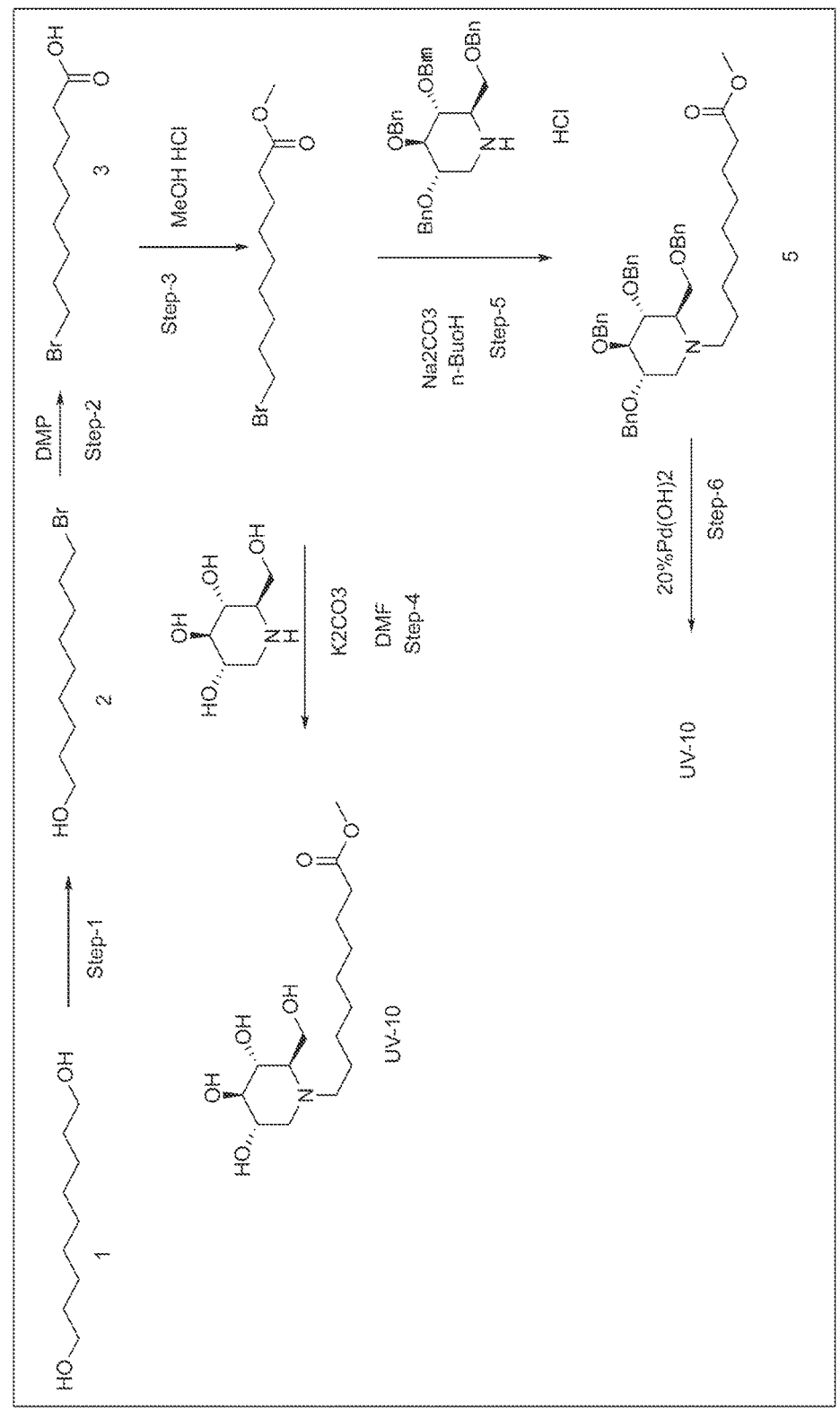

FIG. 17 provides a synthesis scheme for UV-10.

Figure 18:
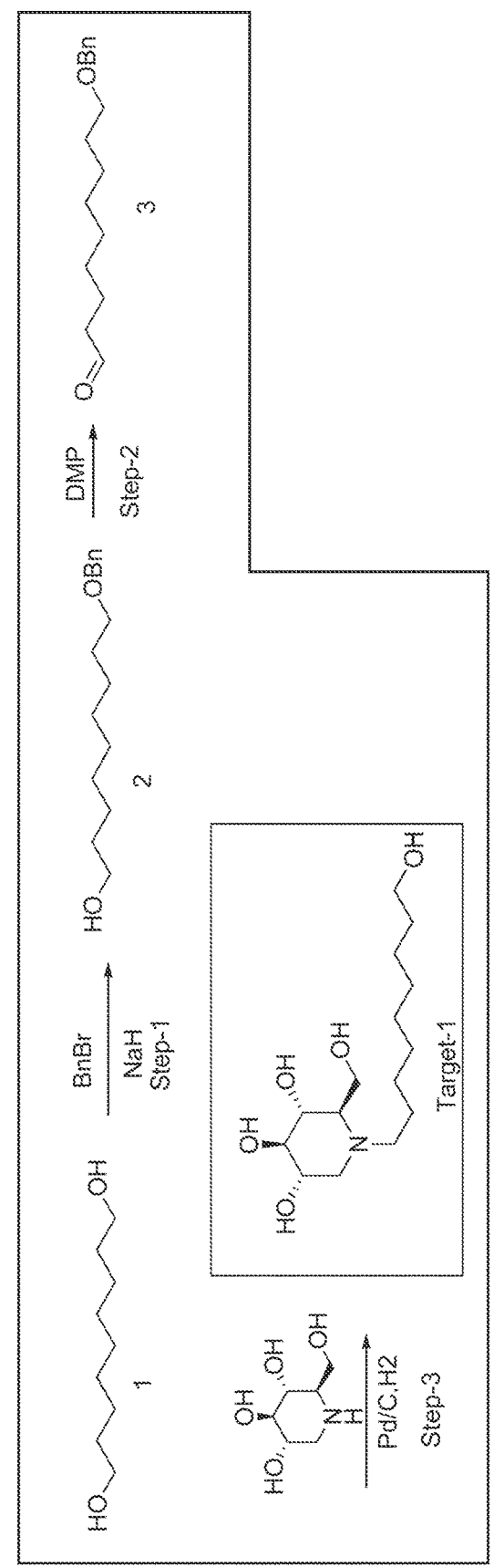

FIG. 18 provides a synthesis scheme for UV-11.

Figure 19:
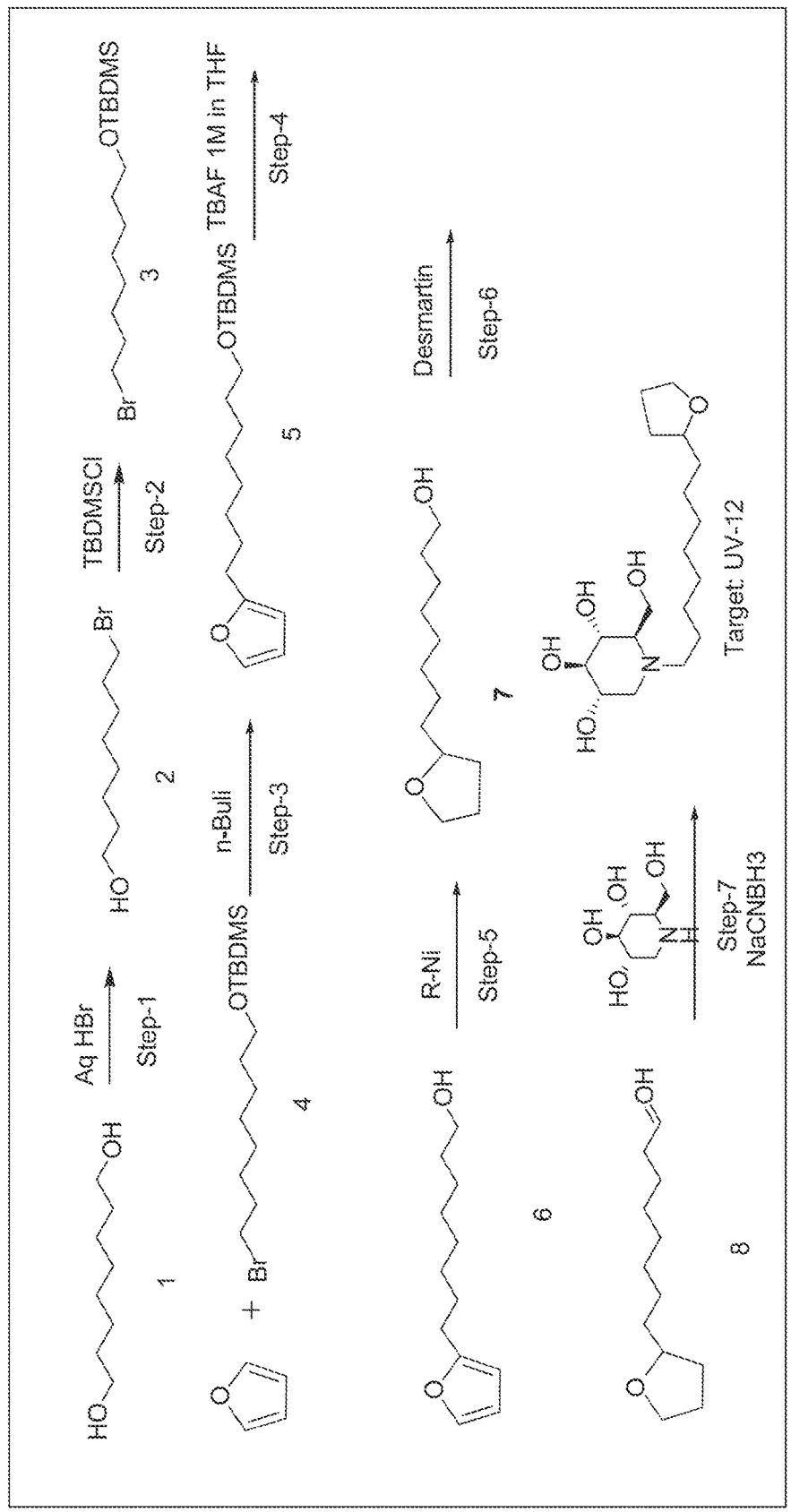

FIG. 19 provides a synthesis scheme for UV-12.

Figure 20:
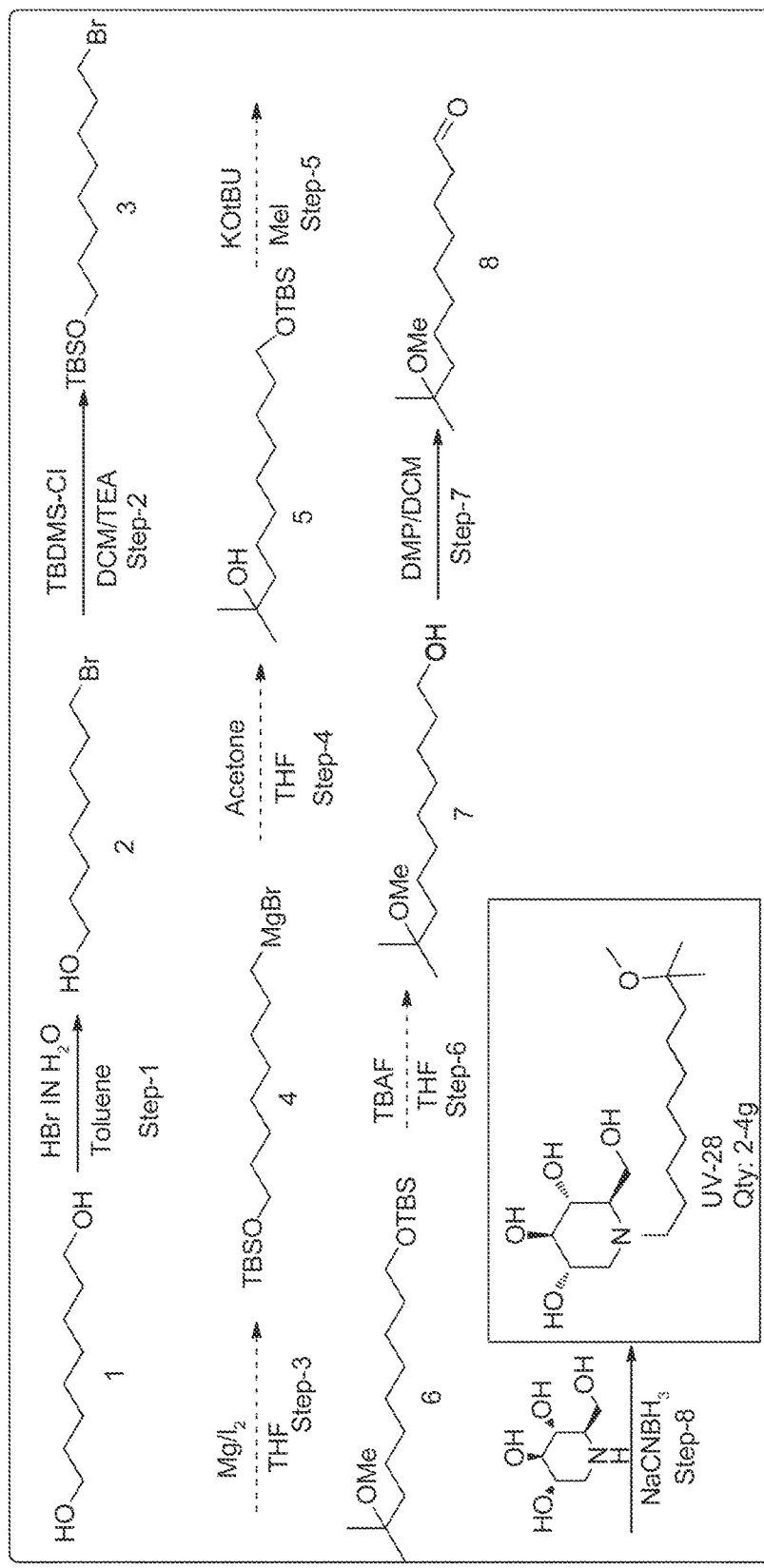

FIG. 20 provides a synthesis scheme for UV-28.

Figure 21:
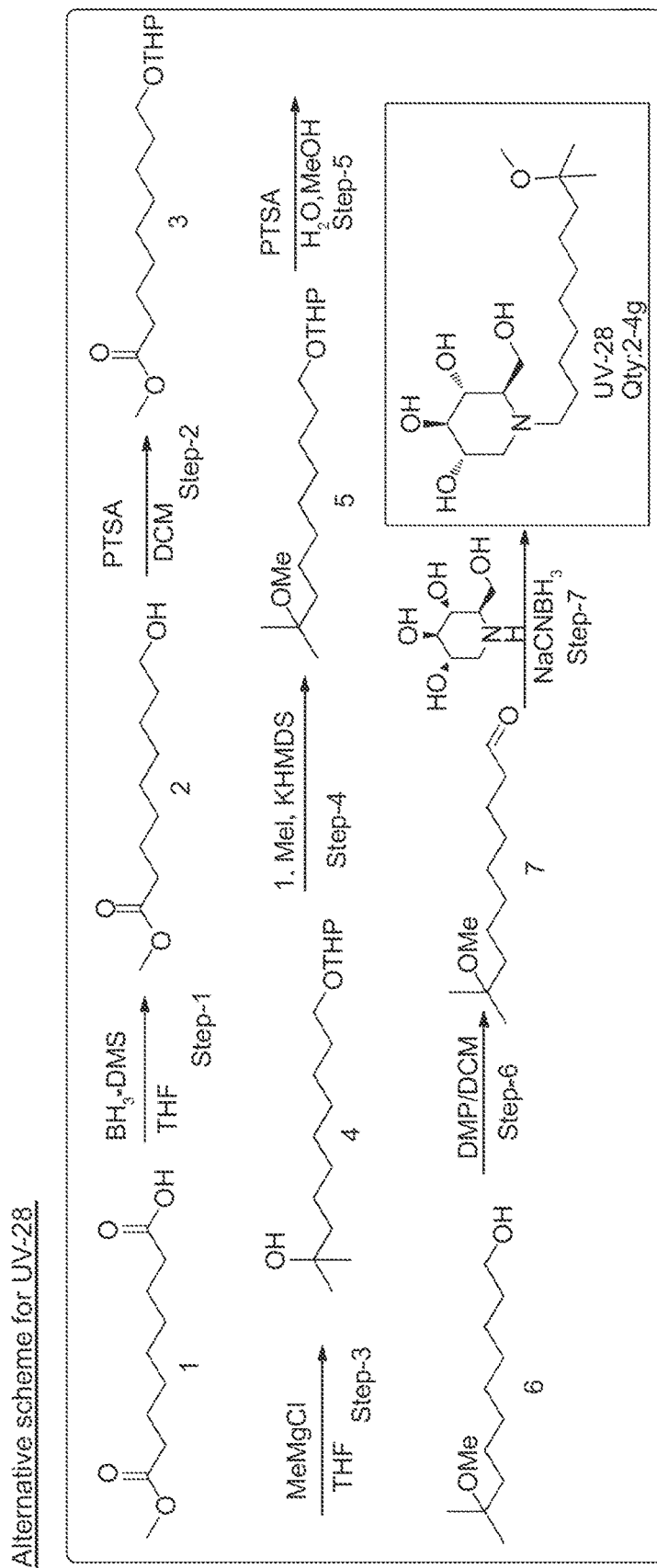

FIG. 21 provides an alternative synthesis scheme for UV-28.

DETAILED DESCRIPTION

Related Documents

The following patent documents, each of which is incorporated herein by reference in its entirety, may be useful for understanding the present disclosure:

U.S. Pat. Nos. 6,545,021; 6,809,803; 6,689,759; 6,465,487; 5,622,972; 7,816,650; 7,256,005; 8,450,345; 7,612,093; and 8,426,445; US patent application publications nos. 20110184019; 20130150405; 20100222384; 20110065754; 20110065753; 20110065752; and 2007-0275998; and U.S. patent application Ser. No. 13/870,341 filed Apr. 25, 2013.

DEFINITION OF TERMS

Unless otherwise specified, "a" or "an" means "one or more."

As used herein, the term "viral infection" describes a diseased state, in which a virus invades a healthy cell, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating or preventing viral infection" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

IC50 or IC90 (inhibitory concentration 50 or 90) is a concentration of a therapeutic agent, such as an iminosugar, used to achieve 50% or 90% reduction of viral load, respectively. LD$_{90}$ stands for (lethal dose 90%) is an estimated dose of an agent at which 90% of the population is expected to die.

DENV stands for Dengue virus.
INFV stands for influenza virus.
IV stands for intravenous.
IG stands for intragastric.
IP stands for intraperitoneal.
PFU stands for a plaque-forming unit.
PBS stands for phosphate buffered saline.
ANOVA stands for an analysis of variance.

DISCLOSURE

The present inventors discovered certain deoxynojirimycin derivatives may be effective against one or more viruses, which may be, for example, a Dengue virus and/or a virus belonging to the Orthomyxoviridae family, such as an Influenza A virus.

In particular, such deoxynojirimycin derivatives may be useful for treating a disease or condition caused by or associated with one or more viruses, which may be, for example, a Dengue virus and/or a virus belonging to the Orthomyxoviridae family, such as an Influenza A virus. In certain embodiments, the deoxynojirimycin derivatives may increase a survival rate or probability for a subject infected with one or more viruses, which may be, for example, a Dengue virus and/or a virus belonging to the Orthomyxoviridae family, such as an Influenza A virus.

Dengue Viruses

Dengue virus belongs to the genus Flavivirus of the Flaviridae family and causes dengue hemorrhagic fever (DHF). Dengue virus includes four closely related serotypes, usually referred to as Dengue 1, Dengue 2, Dengue 3 and Dengue 4. Recovery from infection by one provides lifelong immunity against that serotype but confers only partial and transient protection against infection by the other three. A good evidence exists that sequential infection increases the risk of more serious disease, resulting in DHF. Emerging DHF epidemics are causing increasing concern in the Americas and in Asia, where all four dengue viruses are endemic. DHF has become a leading cause of hospitalization and death among children in several countries. In 2007, there were more than 890,000 reported cases of dengue in the Americas, of which 26,000 cases were DHF.

Dengue is transmitted primarily by the *Aedes aegypti* mosquito and is the most common mosquito-borne viral disease of humans. Globally, 2.5 billion people—40% of the world's population—live in the warm areas where *Aedes aegypti* is common and dengue can be transmitted. The rapid growth of tropical cities and their human and mosquito populations is bringing ever greater numbers of people into contact with this vector. The geographical spread of both the mosquito vectors and the virus has led to a global resurgence of epidemic dengue fever and the emergence of dengue hemorrhagic fever (DHF).

Orthomyxoviridae Family

The Orthomyxoviridae family is a family of RNA viruses that includes live genera:

Influenzavirus A, Influenzavirus B, Influenzavirus C, Isavirus and Thogotovirus. The first three genera contain viruses that can cause influenza in vertebrates, including birds, humans and other mammals.

The Influenzavirus A genus includes a single species, which can causes influenza in birds and certain mammals, including humans, pigs, felines, canines and equines.

Influenza A viruses are negative sense, single-stranded, segmented RNA viruses. Several subtypes of Influenza A virus exist, labeled according to an H number (for the type of hemagglutinin) and an N number (for the type of neuraminidase). Currently known 16 different H antigens (H1 to H16) and nine different N antigens (N1 to N9). Serotypes and subtypes of Influenza A include H1N1 Influenza A; H1N2 Influenza A; H2N2 Influenza A; H3N1 Influenza A; H3N2 Influenza A; H3N8 Influenza A; H5N1 Influenza A; H5N2 Influenza A; H5N3 Influenza A; H5N8 Influenza A; H5N9 Influenza A; H5N9 Influenza A: H7N1 Influenza A; H7N2 Influenza A; H7N3 Influenza A; H7N4 Influenza A; H7N7 Influenza A; H9N2 Influenza A; H10N7 Influenza A.

The Influenzavirus B genus includes a single species, which can cause influenza in humans and seals.

The Influenzavirus C genus includes a single species, which can cause influenza in humans and pigs.

Deoxynojirimycin Derivatives

In some embodiments, the deoxynojirimycin derivative may be a compound belonging to a genus defined by formula (I):

(I)

[Chemical structure showing piperidine ring with $W_1O$, $OW_2$, $OW_3$, $OW_4$ substituents, N-linked alkyl chain terminating in $R_1$, $R_2$, $R_3$ and O]

such that $W_{1-4}$ and $R_{1-3}$ are each independently selected from hydrogen and $C_{1-3}$ alkyl groups, where at least one of $R_{1-3}$ is not hydrogen. $C_{1-3}$ alkyl groups include methyl, ethyl and propyl. In some embodiments, $R_2$ and $R_3$ may be such that they form together one of the following groups: —CH$_2$—, —CH$_2$—CH$_2$— or —CH$_2$—CH$_2$—CH$_2$—.

A compound of formula (I) with each of $W_{1-4}$ and $R_{1-3}$ being hydrogen is N-(9-Methoxynonyl) deoxynojirimycin, which is also known as N9-DNJ or UV-4. The compounds of the defined above genus may be viewed as derivatives of UV-4. The compounds of the defined above genus, such as compounds UV-12 and UV-28 (see FIGS. 13-14) may have one or more advantages compared to other derivatives of UV-4, such as, for example, compounds UV-8, UV-9, UV-10 and UV-11 (see FIG. 13). For example, the compounds of the defined above genus, such as compounds UV-12 and UV-28 may be more efficient compared to other derivatives of UV-4, such as UV-8, UV-9, UV-10 and UV-11, against one or more viruses, which may be, for example, a Dengue virus and/or a virus belonging to the Orthomyxoviridae family, such as an Influenza A virus.

UV-4 derivatives, such as UV-8, UV-9, UV-10, UV-11, UV-12 and UV-28, may be synthesized as depicted in FIGS. 15-21.

Methods of synthesizing deoxynojirimycin derivatives are also disclosed, for example, in U.S. Pat. Nos. 5,622,972, 5,200,523, 5,043,273, 4,994,572, 4,246,345, 4,266.025, 4,405,714, and 4,806,650 and U.S. Patent application publication no. 2007/0275998, which are all incorporated herein by reference.

In some embodiments, the deoxynojirimycin derivative may be in a form of a salt derived from an inorganic or organic acid. Pharmaceutically acceptable salts and methods for preparing salt forms are disclosed, for example, in Berge et al. (*J. Pharm. Sci* 66:1-18, 1977). Examples of appropriate salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

In some embodiments, the deoxynojirimycin derivative may be also used in a form of a prodrug. Prodrugs of DNJ derivatives, such as the 6-phosphorylated DNJ derivatives, are disclosed in U.S. Pat. Nos. 5,043,273 and 5,103,008.

In some embodiments, the deoxynojirimycin derivative may be used as a part of a composition, which further comprises a pharmaceutically acceptable carrier and/or a component useful for delivering the composition to an animal. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

In some embodiments, the pharmaceutical composition may consist essentially of N-substituted deoxynojirimycin, which may mean that the N-substituted deoxynojirimycin is the only active ingredient in the composition.

Yet in some embodiments, N-substituted deoxynojirimycin may be administered with one or more additional antiviral compounds.

In some embodiments, the deoxynojirimycin derivative may be used in a liposome composition, such as those disclosed in US publications nos. 2008/0138351, 2009/0252785 and 2010/0266678.

The DNJ derivative may be administered to a cell or an animal affected by a virus. The DNJ derivative may inhibit morphogenesis of the virus, or it may treat the individual. The treatment may reduce, abate, or diminish the virus infection in the animal.

In some embodiments, the animal may be an animal infected with a Dengue virus which may be a vertebrate, such as a mammal, which may be, for example, a rodent or a primate, such as a human.

In some embodiments, the amount of the DNJ derivative administered to an animal or to an animal cell to the methods of the invention may be an amount effective to inhibit the morphogenesis of Dengue virus from the cell. The term "inhibit" as used herein may refer to the detectable reduction and/or elimination of a biological activity exhibited in the absence of the iminosugar. The term "effective amount" may refer to that amount of the DNJ derivative necessary to achieve the indicated effect. The term "treatment" as used herein may refer to reducing or alleviating symptoms in a subject, preventing symptoms from worsening or progressing, inhibition or elimination of the causative agent, or prevention of the infection or disorder related to the Dengue virus in a subject who is free therefrom.

In some embodiments, the animals may be an animal infected with a virus that belongs to the Orthomyxoviridae family, which may be a vertebrate, such as a bird or a mammal, including primates, such as humans; felines; equines, and canines.

In some embodiments, the amount of the DNJ derivative administered to an animal or to an animal cell to the methods of the invention may be an amount effective to inhibit the morphogenesis of a virus belonging to the Orthomyxoviridae family from the cell. The term "inhibit" as used herein may refer to the detectable reduction and/or elimination of a biological activity exhibited in the absence of the DNJ derivative. The term "effective amount" may refer to that amount of the DNJ derivative necessary to achieve the indicated effect. The term "treatment" as used herein may refer to reducing or alleviating symptoms in a subject, preventing symptoms from worsening or progressing, inhibition or elimination of the causative agent, or prevention of the infection or disorder related to the virus belonging to the Orthomyxoviridae family in a subject who is free therefrom.

Treatment of the disease caused by or associated with a virus, which may be, for example, a Dengue virus or a virus belonging to the Orthomyxoviridae family, such as Influenza A virus, may include destruction of the infecting agent, inhibition of or interference with its growth or maturation, and neutralization of its pathological effects. The amount of the DNJ derivative, which may be administered to the cell or animal is preferably an amount that does not induce toxic effects which outweigh the advantages which accompany its administration.

Actual dosage levels of active ingredients in the pharmaceutical compositions may vary so as to administer an amount of the active compound(s) that is effective to achieve the desired therapeutic response for a particular patient.

The selected dose level may depend on the activity of the DNJ derivative, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated. The adult human daily dosage may range from between about one microgram to about one gram, or from between about 10 mg and 100 mg, of the DNJ derivative per 10 kilogram body weight. In some embodiments, a total daily dose may be from 0.1 mg/kg body weight to 100 mg/kg body weight or from 1 mg/kg body weight to 60 mg/kg body weight or from 2 mg/kg body weight to 50 mg/kg body weight or from 3 mg/kg body weight to 30 mg/kg body weight. The daily dose may be administered over one or more administering events over day. For example, in some embodiments, the daily dose may be distributed over two (BID) administering events per day, three administering events per day (TID) or four administering events (QID). In certain embodiments, a single administering event dose ranging from 1 mg/kg body weight to 10 mg/kg body weight may be administered BID or TID to a human making a total daily dose from 2 mg/kg body weight to 20 mg/kg body weight or from 3 mg/kg body weight to 30 mg/kg body weight. Of course, the amount of the DNJ derivative which should be administered to a cell or animal may depend upon numerous factors well understood by one of skill in the art, such as the molecular weight of the DNJ derivative and the route of administration.

Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the DNJ derivative, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the DNJ derivative. Such pharmaceutical compositions may be administered by a number of routes. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered a in a single dose or in multiple doses which are administered at different times. Because the inhibitory effect of the composition upon a virus may persist, the dosing regimen may be adjusted such that virus propagation is retarded while the host cell is minimally effected. By way of example, an animal may be administered a dose of the composition of the invention once per week, whereby virus propagation is retarded for the entire week, while host cell functions are inhibited only for a short period once per week.

Embodiments described herein are further illustrated by, though in no way limited to, the following working examples.

WORKING EXAMPLES

Example 1

Efficacy of UV-12 and UV-28 Against INFV A/Texas/36/91 (H1N1) Challenge in Mice

Study Summary: This study tested the ability of iminosugars UV-12 and UV-28 to protect mice from lethal influenza infection (~1LD$_{90}$ of influenza A/Texas/36/91 (H1N1) administered intranasally). Compounds were delivered 30-60 minutes prior to viral challenge via the oral (IG) route at 100 or 40 mg/kg and continued three times daily for 10 days. The mice used were ~20 gram, 6-8 week old female BALB/c mice in groups of 10 for efficacy (a summary of the study groups is shown in Table 1). Temperature and weights were taken daily. Endpoint was day 14 post infection, death, or euthanasia. Animals displaying severe illness as determined by >30% weight loss, extreme lethargy, or paralysis were euthanized.

I. Introduction

Purposed: This study aimed to determine the efficacy of small molecules UV-12 and UV-28 in vivo against a lethal influenza A/Texas/36/91 (H1N1) infection.

II. Materials and Methods

Materials

TABLE 1

Test articles

| Name | Amount (mg) | Solvent |
|---|---|---|
| UV-12 | 20 or 8 mg/ml | water |
| UV-28 | 20 or 8 mg/ml | water |

TABLE 2

Viruses for challenge

| Name | Strain | Stock titer | Additional Info |
|---|---|---|---|
| Influenza | A/Texas/36/91 (H1N1) | $2.6 \times 10^5$ PFU/ml | 100 ul of a 1:500 viral dilution was given to mice for ~52 PFU/mouse |

TABLE 3

Animals used

| Species | Strain | Age | Sex | Vendor | Additional Info |
|---|---|---|---|---|---|
| Mouse | BALB/c | 6-8 weeks | F | Charles River | n = 10 per group |

TABLE 4

Equipment

| Item | Vendor |
|---|---|
| Syringes | BD |
| Animal Housing | InnoVive |
| Biodata chips and scanner | Bio Medic Data Systems |
| Ohause scale | Ohause |

Study Design

This study tested the ability of UV-12 and UV-28 to protect mice from lethal influenza infection. The mice used were 6-8 week old female BALB/c mice in groups of 10 (see Table 5 below). Mice were treated with 100 or 40 mg/kg three times daily (TID) via IG route starting approximately 30-60 minutes prior to challenge. Mice were challenged with ~1 LD90 of influenza A/Texas/36/91 (H1N1) administered intranasally (IN). Endpoint was day 14 post infection, death, or euthanasia. Animals displaying severe illness as determined by >30% weight loss, extreme lethargy, or paralysis were euthanized. Temperature and weights were taken daily.

TABLE 5

Mouse groups for the study. The time point of initial dosing (treatment start relative to the infection), dosing regimen and the dose levels/routes are listed.

| Group (n = 10) | Test Article | Dosage, TID | Readouts (After ~1 $LD_{90}$ of influenza A/Texas/36/91 (H1N1) administered intranasally) |
|---|---|---|---|
| 1 | Water | Vehicle Only | Endpoint is day 14 post infection, severe morbidity, death, or >30% weight loss. Animals displaying severe illness (as determined by >30% weight loss, extreme lethargy, or paralysis) will be euthanized. Health assessments, weights and temperature to be taken daily for 15 days total (days 0-14 post infection) |
| 2 | UV-12 | 100 mg/kg | |
| 3 | | 40 mg/kg | |
| 4 | UV-28 | 100 mg/kg | |
| 5 | | 40 mg/kg | |

Standard Protocols

Standard Protocol for Intranasal Infection of Mice

1. Female 6-8 week old BALB/c mice were housed in groups of 5 mice. Mice were quarantined at the study site (Noble Life Sciences, Gaithersburg, Md.) for at least 3 days prior to the start of the study.
2. Food and water was provided ad libitum.
3. The groups of mice challenged with INFV were infected via intranasal (IN) inoculation with ~1×$LD_{90}$ in 100 μL of a 1:500 dilution of INFV in PBS under light anesthesia (Isoflurane).
4. After the infection, mice were placed back into their cages for observation and subsequent dosing.

Protocol for Oral Gavage of Mice for Test Article Delivery

1. Mice were treated with 100 or 40 mg/kg of test article given by the IG route in 100 μL of water (see Table 5 for dosing regimens) three times daily for 10 days.
2. After dosing, mice were returned to their cages and monitored for any distress related to dosing.

Observation of Mice

1. Mice were observed through 13 days post infection (14 days total, 0-13 days post infection).
2. Mice were weighed daily on an Ohause scale and the weights were recorded.
3. All animals had chips implanted at least 3 days prior to virus challenge that monitored the body temperature. The temperatures were recorded daily.

4. Survival and health of each mouse was evaluated once time a day using a scoring system of 1-7.

TABLE 6

Scoring system

| Score | Initials | Description | Appearance | Mobility | Attitude |
|---|---|---|---|---|---|
| 1 | H | Healthy | Smooth Coat. Bright Eyes. | Active, Scurrying, Burrowing | Alert |
| 2 | SR | Slightly Ruffled | Slightly Ruffled coat (usually only around head and neck) | Active, Scurrying, Burrowing | Alert |
| 3 | R | Ruffled | Ruffled Coat throughout body. A "wet" appearance. | Active, Scurrying, Burrowing | Alert |
| 4 | S | Sick | Very Ruffled coat. Slightly closed, inset eyes. | Walking, but no scurrying. | Mildly Lethargic |
| 5 | VS | Very Sick | Very Ruffled Coat. Closed, inset eyes. | Slow to no movement. Will return to upright position if put on its side. | Extremely Lethargic |
| 6 | E | Euthanized | — | — | — |
| 7 | FD | Found Dead | — | — | — |

III. Results

Survival

Mice were infected with a ~1LD$_{90}$ of influenza A/Texas/36/91 (H1N1) and treated with 100 or 40 mg/kg of UV-12 or UV-28 three times daily for 10 days. Survival in each infected treatment group, calculated as percent survival versus days post-infection, is shown in FIG. 1 and Table 7. The infected groups which were treated with 100 mg/kg of both UV-12 and -28 showed 100% survival. The infected groups that were treated with 40 mg/kg of UV-12 and -28 displayed 20 and 60% survival, respectively. The untreated control group showed 0% survival and was all 'found-dead' or 'euthanized' by day 7 post-infection.

FIG. 1 is a plot presenting survival data of infected mice grouped by treatment. Table 7 presents results of analysis of survival of infected mice. The survival data plotted in FIG. 1 were analyzed using the Mantel-Cox (Log rank) test in GraphPad Prism.

TABLE 7

| Group | Mean Survival (Days) | % Survival | P value to water control |
|---|---|---|---|
| Water | 7 | 0 | N/A |
| UV-12 100 mg/kg | >13 | 100 | <0.0001 |
| UV-12 40 mg/kg | 9 | 20 | <0.0001 |
| UV-28 100 mg/kg | >13 | 100 | <0.0001 |
| UV-28 40 mg/kg | >13 | 60 | <0.0001 |

Biometric Analysis

During the course of this study, individual weights, health scores, and temperatures were monitored daily for each group. The average weights for each group of mice are shown in FIG. 2. Every animal was tagged with a chip to perform daily temperature readings using a BMDS scanner; the average temperatures are shown in FIG. 3. The health scores are shown is FIG. 4.

Conclusions

Influenza-infected mice were treated with 100 or 40 mg/kg of UV-12 or UV-28 via oral gavage three times daily for 10 days. Both groups that were treated with 100 mg/kg showed 100% survival, and groups that were treated with 40 mg/kg showed 60 and 20% survival for UV-28 and UV-12, respectively. While UV-28 did appear to show better efficacy at 40 mg/kg, it appears to be more toxic than UV-12 (FIG. 4). While mice that were treated with 100 mg/kg of UV-12 fully recovered from the infection and returned to normal, mice that were treated with 100 mg/kg of UV-28 never recovered their health score and remained 'ruffled' for the entire course of the study. In combination with a higher health score, indicating morbidity, the mice that were treated with UV-28 did not recover their weight as well, while mice treated with UV-12 almost completely recovered. Mice that were treated only with vehicle all succumbed to infection by day 7 post-infection, displaying 0% survival.

Example 2

Survival Analysis of UV-12 in A129 ADE Model

Purpose: This study determined the efficacy of UV-12 in promoting survival of mice challenged with dengue virus. Compound were given by the oral route (3× per day intragastric via oral gavage—IG) for a total number of 7 days after the start of dosing. The experiment used the A129 ADE model of infection. (Prestwood T R, Morar M M, Zellweger R M, Miller R, May M M, Yauch L E, Lada S M. Shresta S. Gamma interferon (IFN-γ) receptor restricts systemic dengue virus replication and prevents paralysis in IFN-α/β receptor-deficient mice. J Virol. 2012 December; 86(23): 12561-70.) Animals received the virus challenge dose ~1 LD$_{90}$ on day 0. The first dose was given 0.5-1 hr pre-virus challenge. Survival was measured until 30 days after infection.

Iminosugar candidate: UV-12.

Experimental Design for the Study:

Control, H$_2$O=DENV (S221) [10 mice]

UV-12, (100 mg/kg/dose)+DENV (S221) [10 mice]

Mice: Sex matched 5-6 weeks old A129 (129/SV IFN-α, -β receptor$^{-/-}$)

Administration Route:

Iminosugar: Orally 3× day, (gavage (IG)) every 8 hours

Antibody: IP

Virus: IV

Antibody and Iminosugar Compound were given simultaneously, then virus within 30 minutes
Virus Challenge:
Antibody: 100 μg 2H2 (IgG2a anti-DENV1-4 prM) from ATCC, day 0 and day 1 in 40 ul
Virus: DENV2 Strain S221 (v512) (Zellweger R M, Prestwood T R, Shresta S.
Enhanced infection of liver sinusoidal endothelial cells in a mouse model of antibody-induced severe dengue disease. Cell Host Microbe. 2010 Feb. 18; 7(2):128-39)
Dose: 1E11 GE (genomic equivalents) per animal
Read-out:
Animal survival. Animals displaying severe illness (as determined by 20% weight loss, extreme lethargy, ruffled coat, or paralysis) are euthanized.
Resources:
A129 mice, 2H2 antibody, and S221 virus were supplied by Sujan Shresta, La Jolla Institute for Allergy and Immunology
Supplied by Unither Virology: UV-12
FIG. 5 presents results of this study. Mice were treated with UV-12 diluted in 50 ul, water orally, three times per day for a total of 7 days. Initiation of treatment was 1 hr before virus intravenous challenge. UV-12 treated A129 mice displayed an increased survival compared to control animals that was only orally administered 50 uL of water three times per day.

Example 3

Efficacy of Selected Iminosugars in Mice; Influenza A/Texas/36/91 (H1N1) Challenge Study Summary: This study analyzed the toxicity and efficacy of UV-8, UV-9, UV-10, UV-11, and UV-12 in mice during an H1N1 influenza infection. Previously, studies that were performed with oral delivery of UV-4B ter in die (TID) at 100 mg/kg resulted in efficacy against H1N1 and did not show any discernible signs of toxicity. In the current study, we examined delivery doses of UV-4B. UV-8, UV-9, UV-10. UV-11 and UV-12 at 100 mg/kg, delivered ter in die by the oral route (intragastric via oral gavage or IG. Small groups (n=3) that were included to examine gross toxicity received 100 mg/kg of the iminosugars but without a viral challenge. UV-4B, UV-8. UV-9, UV-10. UV-11 or UV-12 was delivered to the animals starting at 1 hour before intranasal infection (IN) with ~1 $LD_{90}$ of influenza A/Texas/36/91 (H1N1). Animals were then treated TID for 10 days total (days 0-9 post infection). Efficacy was evaluated by comparing survival, temperature changes, and weight gain/loss to an infected untreated control group. Mice dosed with UV-8, -9, -10, or -11 did not show any improvement in survival over the untreated control group, while the group dosed with UV-12 and the positive control group dosed with UV-4B both showed a significant increase in survival.

I. Introduction

This study aimed to determine the efficacy of UV-8. UV-9, UV-10, UV-11, and UV-12 when administered orally at 100 mg/kg TID against a lethal intranasal infection with influenza virus A/Texas/36/91 (H1N1) in the BALB/c mouse model. In addition to the efficacy arm, each of the iminosugars was tested in a small group of animals with the same treatment regimen (100 mg/kg, oral gavage, TID) in the absence of a viral infection to examine gross toxicity of each analog (general health, weight, temperature, and mortality evaluations).

II. Materials and Methods

Materials

TABLE 8

Test articles

| Name | Concentration | Solvent | Additional Info |
|------|--------------|---------|-----------------|
| UV-4B | 100 mg/kg (2 mg/dose) | $H_2O$ | HCl salt |
| UV-8 | 100 mg/kg (2 mg/dose) | | |
| UV-9 | 100 mg/kg (2 mg/dose) | | |
| UV-10 | 100 mg/kg (2 mg/dose) | | |
| UV-11 | 100 mg/kg (2 mg/dose) | | |
| UV-12 | 100 mg/kg (2 mg/dose) | | |

TABLE 9

Viruses for Challenge

| Name | Strain | Stock titer |
|------|--------|-------------|
| Influenza A virus | A/Texas/36/91 (H1N1) | $2.8 \times 10^5$ PFU/mL |

TABLE 10

Animals used

| Species | Strain | Age | Sex | Vendor | Additional Info |
|---------|--------|-----|-----|--------|-----------------|
| Mouse | BALB/c | 4-6 weeks | F | Charles River | 7 groups n = 10<br>5 groups n = 3 |

TABLE 11

Equipment

| Item | Vendor |
|------|--------|
| Syringes | BD |
| Animal Housing | InnoVive |
| Plastic Feeding Tubes | Instech Solomon |
| Biodata chips and scanner | Bio Medic Data Systems |
| Ohause scale | Ohause |

Study Design

UV-8, -9, -10, -11, -12, and UV-4B were prepared in $H_2O$ at 20 mg/ml for a delivery dose of 100 mg/kg, assuming ~20 g mice given 0.1 mL of compound. Groups of BALB/c mice were treated at one hour before (−1 h) intranasal infection with ~1 $LD_{90}$ of INFV A/Texas/36/91 (H1N1) and then compounds were administered three times daily for a total of 10 days (see Table 12 for study design summary). Weights, temperature, and survival were monitored and used for evaluation of protective efficacy and toxicity of each analog.

TABLE 12

Mouse groups for the study. The time point of initial dosing (treatment start relative to the infection), dosing regimen and the dose levels/routes are listed. Mice were dosed once or twice per day for total of 10 days.

| Group | Mouse Strain | N | Treatment | Delivery route/frequency on days 0-9 (10 days total starting at 1 h before infection) | Challenge | Readouts |
|---|---|---|---|---|---|---|
| 1 | Female BALB/C 4-6 weeks of age | 10 | Vehicle | IG 100 ul, TID | 1 $LD_{90}$ of Influenza A/Texas/36/91 (H1N1) | Endpoint is day 14, death, or >30% weight loss. Animals displaying severe illness (as determined by >30% weight loss, extreme lethargy, or paralysis) will be euthanized. Temperature and weights to be taken daily for 14 days |
| 2 | | 10 | 100 mg/kg UV-4B | | | |
| 3 | | 10 | 100 mg/kg UV-8 | | | |
| 4 | | 10 | 100 mg/kg UV-9 | | | |
| 5 | | 10 | 100 mg/kg UV-10 | | | |
| 6 | | 10 | 100 mg/kg CV-11 | | | |
| 7 | | 10 | 100 mg/kg UV-12 | | | |
| 8 | | 3 | 100 mg/kg UV-8 | | None (Toxicity assessment) | |
| 9 | | 3 | 100 mg/kg UV-9 | | | |
| 10 | | 3 | 100 mg/kg UV-10 | | | |
| 11 | | 3 | 100 mg/kg CV-11 | | | |
| 12 | | 3 | 100 mg/kg UV-12 | | | |

Standard Protocols

Standard Protocol for Intranasal Infection of Mice

1. Female 4-6 week old BALB/c mice were housed in groups of 3-5 mice. Mice were quarantined at the study site (Noble Life Sciences, Gaithersburg, Md.) for at least 3 days prior to the start of the study.
2. Food and water was provided ad libitum.
3. The groups of mice challenged with influenza were anesthetized with 5% Isofluorene and maintained at 2.5% prior to intranasal inoculation with ~1 $LD_{90}$ of INFV in 100 μL PBS.
4. After the infection mice were placed back into their cages for observation and dosing.

Protocol for Oral Gavage or Injection of Mice for Compound Delivery

1. Mice were treated starting at 1 hour before infection with 100 μL of compound in $H_2O$ (see Table 12 for dosing regimens) three times a day for 10 days total with 100 mg/kg of UV-4B, UV-8, UV-9, UV-10, UV-11, or UV-12 compound given by the oral route (intragastric via oral gavage).
2. After dosing, mice were returned to their cages and monitored for any distress related to dosing.

Observation of Mice

1. Mice were observed through 13 days post infection (14 days total, 0-13 days post infection).
2. Mice were weighed daily on an Ohause scale and the weights were recorded.
3. All animals had chips implanted that monitored the body temperature. The temperatures were recorded daily.
4. Survival and health of each mouse was evaluated three times a day using a scoring system of 1-7.
5. Mice were euthanized when scored at 5 or above (Very Sick; Very Rufftled Coat; Closed, inset eyes; Slow to no movement; Will return to upright position if put on its side; extremely lethargic).

III. Results

Survival

Mice were infected with a ~1 $LD_{90}$ of Influenza virus A/Texas/36/91 (H1N1) one hour after their first dose of UV-4R or UV-4 analogs, as outlined above. Survival tables, calculated as percent survival versus days post-infection, are shown in FIG. 6. As expected based on previous studies, groups that were dosed orally TID with UV-4B at 100 mg/kg showed a survival rate of 100% and a MTD of >13 days (FIG. 7). Mice that were dosed orally with UV-12 at 100 mg/kg showed a survival rate of 90%, and a MTD of >13 days (FIG. 6, 7). Mice treated with UV-8, UV-9, UV-10, or UV-11 displayed a MTD of 10.5, 7, 7.5, and 8 days, respectively, and survival rates of 0% with the exception of UV-8 (30%) (FIG. 6, 7). Negative control mice dosed with vehicle (H2O) demonstrated 30% survival and a MID of 9 days (FIGS. 6, 7).

Mice which received UV-8, -9, -10, -11, or -12 at 100 mg/kg without a viral challenge to examine gross toxicity displayed 100% survival (data not shown).

Biometric Analysis

During the course of this study, individual weights and temperatures were monitored daily for each group. The average weights for each group of mice are shown in FIG.

8 with statistical analysis shown in FIG. 9. The average temperatures are shown in FIG. 10 with statistical analysis shown in FIG. 11.

As a second biometrics the animals' temperatures were evaluated. Every animal was tagged with a chip to perform daily temperature readings using a scanner. The graphs in FIG. 10 show the body temperatures for each test group. Significance shown against the vehicle control is indicated in FIG. 11.

Conclusions

The group of infected mice dosed orally TID with 100 mg/kg of UV-4B exhibited 100% survival, where the groups which were orally dosed with 100 mg/kg of UV-9, UV-10, and UV-11 exhibited 0% survival. Statistical analysis on weights and temperatures for these groups was not performed due to a lower survival rate and MTD than the vehicle control. Mice dosed orally with UV-8 exhibited 30% survival, and thus no significant difference from the vehicle control group. Mice dosed orally with 100 mg/kg of UV-12 exhibited 90% survival, as well as significant increases in overall temperature and weight. UV-12 also showed mild toxicity with steady weight loss in the uninfected group, but uninfected mice dosed with UV-12 did not lose more than 10% weight overall and they were able to fully recover after the dosing regimen had been completed. Statistical analysis was not performed on any of the parameters examined for the uninfected groups of mice (gross toxicity) as the number of mice per group was limited (n=3) there was no uninfected, undosed control group for comparison.

Example 4

Survival Analysis of UV-4 and UV-12 in ADE Model

Purpose: This study determined the efficacy of UV-4 and UV-12 in promoting survival of mice challenged with dengue virus. All compounds were given by the oral route (3× per day intragastric via oral gavage—IG) for a total number of 7 days after the start of dosing. The experiment used the ADE model of infection developed in the lab (Zellweger et al. CellHostMicrob 7; pp 1-12 (2010)). Animals received the virus challenge dose ~1 $LD_{90}$ on day 0. The first dose was given 0.5-1 hr pre-virus challenge. Survival was measured until 3 days after dosing was completed. UV-4 HCl salt was used in this study, which is equal to "UV-4B".
Iminosugar Candidates:
1. N-9-methoxynonyl-deoxynojirimycin (UV-4) (HCl Salt), UV-4B
2. UV-12
3. Control, $H_2O$
Experimental Design for the Study
1. Control, H2O+DENV (S221) [7 mice]
2. UV-4, 1 mg (50 mg/kg/dose)+DENV (S221) [5 mice]
3. UV-12, 1 mg (50 mg/kg/dose)+DENV (S221) [5 mice]
Mice: Sex Matched 5-6 Weeks Old
 AG 129 (129/SV IFN-α,β, and γ-receptor−/−) breeded at LIAI by Sujan Shresta (also publically available by The Jackson Laboratory, Bar Harbor, Me.)
Route:
Iminosugar: Orally 3× day, (gavage (IG)) every 8 hours
Antibody: IP (Intraperitoneal)
Virus: IV
Antibody and Compound were given simultaneously, then virus within 30 minutes Virus Challenge:
Antibody: 5 μg 2H2 (anti-prM) available from ATCC
Virus: DENV2 Strain S221 (v476) (Zellweger R M, Prestwood T R, Shresta S.
 Enhanced infection of liver sinusoidal endothelial cells in a mouse model of antibody-induced severe dengue disease. Cell Host Microbe. 2010 Feb. 18; 7(2):128-39)
Dose: 1E9 GE (genomic equivalents) per animal
Read-out:
 Animal survival. Animals displaying severe illness (as determined by 20% weight loss, extreme lethargy, ruffled coat, or paralysis) were euthanized.
 FIG. 12 presents results of this study. All groups were treated with the same dose of compounds:
Experimental Design for the Study
1. Control, H2O+DENV (S221) [7 mice]
2. UV-4, 1 mg (50 mg/kg/dose)+DENV (S221) [5 mice]
3. UV-8, 1 mg (50 mg/kg/dose)+DENV (S221) [5 mice]
4. UV-9, 1 mg (50 mg/kg/dose)+DENV (S221) [5 mice]
5. UV-10, 1 mg (50 mg/kg/dose)+DENV (S221) [5 mice]
6. UV-11, 1 mg (50 mg/kg/dose)+DENV (S221) [5 mice]
7. UV-12, 1 mg (50 mg/kg/dose)+DENV (S221) [5 mice]
 This study was to determine the efficacy of UV-4 and its analogues in promoting survival of mice challenged with dengue virus. All compounds were given by the oral route (3× per day intragastric via oral gavage—IG) for a total number of 7 days after the start of dosing. The experiment used the ADE model of infection (Zellweger et al. CellHost-Microb 7; pp1-12 (2010)). Animals received the virus challenge dose ~1 LD90 on day 0. The first compound dose began 0.5-1 hr pre-virus challenge.

Survival were measured until 3 days after dosing.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:
1. A compound having the formula:

or a pharmaceutically acceptable salt thereof.

2. A pharmaceutical composition comprising a) a pharmaceutically effective amount of the compound according to claim 1 and b) a pharmaceutically acceptable carrier.

3. A method of treating a Dengue viral infection in a subject in need of such treatment comprising administering to the subject an effective amount of a compound having the formula:

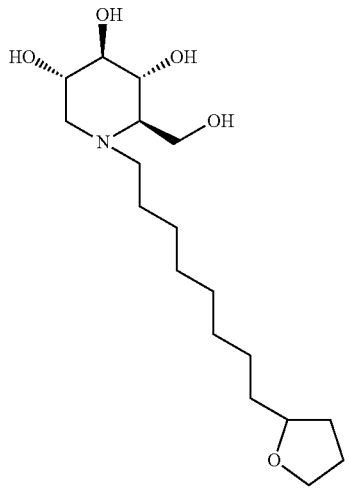 [SMILES: OC[C@@H]1[C@@H](O)[C@H](O)[C@@H](O)CN1CCCCCCCCC1CCCO1]

or a pharmaceutically acceptable salt thereof.

4. The method of claim 3, wherein the dengue viral infection is a Dengue 2 viral infection.

5. The method of claim 3, wherein the subject is a mammal.

6. The method of claim 5, wherein the subject is a human.

7. A method of treating an influenza viral infection in a subject in need of such treatment, comprising administering to the subject an effective amount of a compound having the formula:

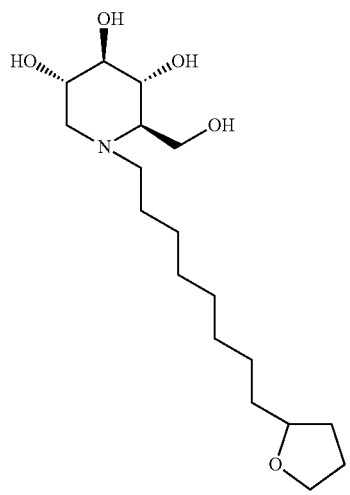 [SMILES: OC[C@@H]1[C@@H](O)[C@H](O)[C@@H](O)CN1CCCCCCCCC1CCCO1]

or a pharmaceutically acceptable salt thereof.

8. The method of claim 7, wherein the virus is an Influenza A virus.

9. The method of claim 8, wherein the virus is a H3N2 subtype of the Influenza A virus.

10. The method of claim 8, wherein the virus is a H1N1 subtype of the Influenza A virus.

11. The method of claim 7, wherein the subject is a mammal.

12. The method of claim 11, wherein the subject is a human being.

* * * * *